(12) United States Patent
Gibson et al.

(10) Patent No.: US 11,583,633 B2
(45) Date of Patent: Feb. 21, 2023

(54) SYSTEMS AND METHODS FOR DELAYED DRUG DELIVERY

(71) Applicant: AMGEN INC., Thousand Oaks, CA (US)

(72) Inventors: Scott Robert Gibson, Granada Hills, CA (US); Adam B. McCullough, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 623 days.

(21) Appl. No.: 15/944,709

(22) Filed: Apr. 3, 2018

(65) Prior Publication Data

US 2019/0298924 A1    Oct. 3, 2019

(51) Int. Cl.
*A61M 5/20* (2006.01)
*A61M 5/315* (2006.01)
(Continued)

(52) U.S. Cl.
CPC ............ *A61M 5/20* (2013.01); *A61M 5/2033* (2013.01); *A61M 5/31515* (2013.01);
(Continued)

(58) Field of Classification Search
CPC ............ A61M 5/2033; A61M 5/31515; A61M 5/31571; A61M 5/5086;
(Continued)

(56) References Cited

U.S. PATENT DOCUMENTS 4,886,499 A   12/1989 Cirelli et al.
5,135,479 A   8/1992 Sibalis et al.
(Continued)

FOREIGN PATENT DOCUMENTS

CN   1476566 A   2/2004
CN   1747683 A   3/2006
(Continued)

OTHER PUBLICATIONS

Thompson, "Market Trends: Disposable Mono-dose Auto-injectors and Pen-injectors", *Drug Delivery Report*, pp. 53-55 (Winter 2007/2008).
(Continued)

*Primary Examiner* — Nathan R Price
*Assistant Examiner* — Justin L Zamory
(74) *Attorney, Agent, or Firm* — Marshall, Gerstein & Borun LLP

(57) ABSTRACT

Systems and methods for delayed delivery of a drug are disclosed. A drug delivery system may include a delivery member for insertion into a patient and a reservoir configured to receive a volume of a drug. An energy source may be activatable by the patient to actuate the reservoir to deliver the drug to the patient as a single bolus. A lockout system may be configured to have a locked state, wherein the lockout system prevents movement of the delivery member and/or activation of the energy source, and an unlocked state, wherein the lockout system permits movement of the delivery member and/or activation of the energy source. The lockout system may be configured to automatically change from the locked state to the unlocked state after a preselected time period has elapsed. An output element may generate a detectable output after the preselected time period has elapsed for notifying the patient.

20 Claims, 12 Drawing Sheets

(51) Int. Cl.
*A61M 5/50* (2006.01)
*A61M 25/06* (2006.01)
*A61M 5/31* (2006.01)
*A61M 5/32* (2006.01)

(52) U.S. Cl.
CPC ...... *A61M 5/31571* (2013.01); *A61M 5/5086* (2013.01); *A61M 25/06* (2013.01); *A61M 2005/2013* (2013.01); *A61M 2005/2026* (2013.01); *A61M 2005/2073* (2013.01); *A61M 2005/3125* (2013.01); *A61M 2005/3143* (2013.01); *A61M 2005/3267* (2013.01); *A61M 2005/5033* (2013.01); *A61M 2205/505* (2013.01); *A61M 2205/581* (2013.01); *A61M 2205/582* (2013.01); *A61M 2205/583* (2013.01); *A61M 2205/587* (2013.01)

(58) Field of Classification Search
CPC .. A61M 2005/2013; A61M 2005/2026; A61M 2005/2073; A61M 2005/3125; A61M 2005/3143; A61M 2005/3267; A61M 2005/5033; A61M 2205/505; A61M 2205/581–583; A61M 2205/587
See application file for complete search history.

(56) References Cited

U.S. PATENT DOCUMENTS

| | | | |
|---|---|---|---|
| 5,250,023 A | 10/1993 | Lee et al. | |
| 5,527,288 A | 6/1996 | Gross et al. | |
| 5,693,016 A | 12/1997 | Gumaste et al. | |
| 5,782,799 A | 7/1998 | Jacobsen et al. | |
| 5,785,688 A | 7/1998 | Joshi et al. | |
| 5,814,020 A | 9/1998 | Gross | |
| 5,820,622 A | 10/1998 | Gross et al. | |
| 5,858,001 A | 1/1999 | Tsals et al. | |
| 5,860,957 A | 1/1999 | Jacobsen et al. | |
| 5,957,895 A | 9/1999 | Sage et al. | |
| 5,997,501 A | 12/1999 | Gross et al. | |
| 6,010,492 A | 1/2000 | Jacobsen et al. | |
| 6,068,613 A | 5/2000 | Kriesel et al. | |
| 6,074,369 A | 6/2000 | Sage et al. | |
| 6,126,637 A | 10/2000 | Kriesel et al. | |
| 6,186,982 B1 | 2/2001 | Gross et al. | |
| 6,387,078 B1 | 5/2002 | Gillespie, III | |
| 6,485,461 B1 | 11/2002 | Mason et al. | |
| 6,530,900 B1 | 3/2003 | Daily et al. | |
| 6,589,229 B1 | 7/2003 | Connelly et al. | |
| 6,595,956 B1 | 7/2003 | Gross et al. | |
| 6,635,049 B1 | 10/2003 | Robinson et al. | |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,723,072 B2 | 4/2004 | Flaherty et al. | |
| 6,740,059 B2 | 5/2004 | Flaherty | |
| 6,749,587 B2 | 6/2004 | Flaherty | |
| 6,768,425 B2 | 7/2004 | Flaherty et al. | |
| 6,824,529 B2 | 11/2004 | Gross et al. | |
| 6,830,558 B2 | 12/2004 | Flaherty et al. | |
| 6,953,446 B2 | 10/2005 | Fischer | |
| 6,955,670 B2 | 10/2005 | Martin et al. | |
| 6,960,192 B1 | 11/2005 | Flaherty et al. | |
| 7,014,625 B2 | 3/2006 | Bengtsson | |
| 7,018,360 B2 | 3/2006 | Flaherty et al. | |
| 7,029,455 B2 | 4/2006 | Flaherty | |
| 7,070,580 B2 | 7/2006 | Nielsen | |
| 7,115,108 B2 | 10/2006 | Wilkinson et al. | |
| 7,128,727 B2 | 10/2006 | Flaherty et al. | |
| 7,137,964 B2 | 11/2006 | Flaherty | |
| 7,137,965 B2 | 11/2006 | Fischer et al. | |
| 7,144,384 B2 | 12/2006 | Gorman et al. | |
| 7,303,549 B2 | 12/2007 | Flaherty et al. | |
| 7,410,476 B2 | 8/2008 | Wilkinson et al. | |
| 7,524,304 B2 | 4/2009 | Genosar | |
| 7,530,964 B2 | 5/2009 | Lavi et al. | |
| 7,537,590 B2 | 5/2009 | Santini, Jr. et al. | |
| 9,061,097 B2 | 6/2015 | Holt et al. | |
| 2002/0040208 A1 | 4/2002 | Flaherty et al. | |
| 2002/0151875 A1 | 10/2002 | Haller | |
| 2003/0014014 A1 | 1/2003 | Nitzan | |
| 2003/0055380 A1 | 3/2003 | Flaherty | |
| 2004/0010207 A1 | 1/2004 | Flaherty et al. | |
| 2004/0015042 A1 | 1/2004 | Vincent et al. | |
| 2004/0054327 A1 | 3/2004 | Gillespie | |
| 2004/0068224 A1 | 4/2004 | Couvillon et al. | |
| 2004/0078028 A1 | 4/2004 | Flaherty et al. | |
| 2004/0092865 A1 | 5/2004 | Flaherty et al. | |
| 2004/0092878 A1 | 5/2004 | Flaherty | |
| 2004/0116866 A1 | 6/2004 | Gorman et al. | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0022274 A1 | 1/2005 | Campbell et al. | |
| 2005/0182366 A1 | 8/2005 | Vogt et al. | |
| 2005/0203461 A1 | 9/2005 | Flaherty et al. | |
| 2005/0234430 A1 | 10/2005 | Mao et al. | |
| 2006/0178629 A1 | 8/2006 | Gillespie et al. | |
| 2006/0178631 A1 | 8/2006 | Gillespie et al. | |
| 2006/0178642 A1 | 8/2006 | Gillespie et al. | |
| 2006/0276771 A1 | 12/2006 | Galley et al. | |
| 2007/0078394 A1 | 4/2007 | Gillespie, III | |
| 2007/0118405 A1 | 5/2007 | Campbell et al. | |
| 2007/0135767 A1 | 6/2007 | Gillespie et al. | |
| 2008/0051738 A1 | 2/2008 | Griffin | |
| 2008/0220092 A1 | 9/2008 | Dipierro et al. | |
| 2009/0093792 A1 | 4/2009 | Gross et al. | |
| 2009/0093793 A1 | 4/2009 | Gross et al. | |
| 2009/0149809 A1* | 6/2009 | Bollenbach | A61M 5/2033 604/111 |
| 2010/0191217 A1* | 7/2010 | Hommann | A61M 5/2033 604/506 |
| 2010/0227818 A1 | 9/2010 | Bock et al. | |
| 2012/0010594 A1* | 1/2012 | Holt | A61M 5/14248 604/506 |
| 2012/0022499 A1 | 1/2012 | Anderson et al. | |
| 2014/0330243 A1* | 11/2014 | Kietzmann | G16H 40/63 604/500 |
| 2017/0049965 A1* | 2/2017 | Baker | A61M 5/20 |

FOREIGN PATENT DOCUMENTS

| | | |
|---|---|---|
| CN | 101238468 A | 8/2008 |
| EP | 2575935 A1 | 4/2013 |
| EP | 3045189 A1 | 7/2016 |
| WO | WO-9948546 A1 | 9/1999 |
| WO | WO-01/58506 A2 | 8/2001 |
| WO | WO-02/40083 A2 | 5/2002 |
| WO | WO-2005039685 A1 | 5/2005 |
| WO | WO-2006/121921 A2 | 11/2006 |
| WO | WO-2007/010522 A1 | 1/2007 |
| WO | WO-2007129317 A1 | 11/2007 |
| WO | WO-2008024814 A2 | 2/2008 |
| WO | WO-2009109344 A1 | 9/2009 |
| WO | WO-2011046950 A1 | 4/2011 |
| WO | WO-2014/066256 A1 | 5/2014 |
| WO | WO-2016/003813 A1 | 1/2016 |
| WO | WO-2017/189089 A1 | 11/2017 |

OTHER PUBLICATIONS

Pegfilgrastim on the same day versus next day of chemotherapy in patients with breast cancer, non-small-cell lung cancer, ovarian cancer, and non-Hodgkin's lymphoma: Results of four multicenter, double-blind, randomized phase II studies. By: Howard A. Burris et al.—as published in May 2010 (found at https://www.ncbi.nlm.nih.gov/pmc/articles/PMC2868638/pdf/jop133.pdf).

(56) References Cited

OTHER PUBLICATIONS

International Application No. PCT/US2019/025318, International Search Report and Written Opinion, dated Jul. 9, 2019.

* cited by examiner

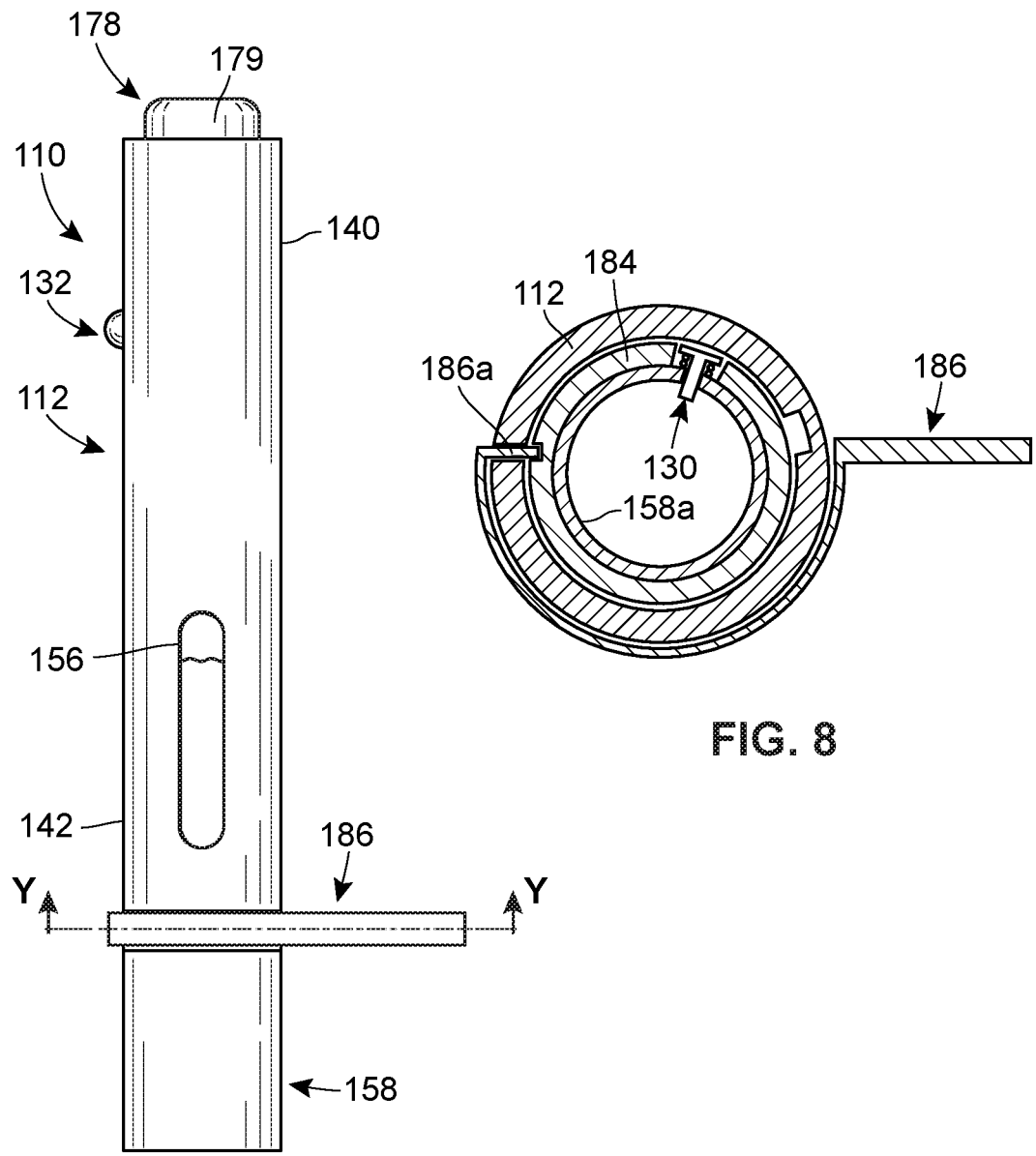

Unused/not ready to Administer

Ready to Administer

SYSTEMS AND METHODS FOR DELAYED DRUG DELIVERY

FIELD OF DISCLOSURE

The present disclosure generally relates to injectors for drug delivery and related methods. More particularly, the present disclosure relates to injectors for use in a treatment regimen benefiting from injection of a drug within a particular timeframe.

BACKGROUND

Parenteral delivery of various drugs, i.e., delivery by means other than through the digestive track, has become a desired method of drug delivery for various reasons. Bypassing the digestive system of the patient can avoid degradation of the active ingredients caused by the catalytic enzymes in the digestive tract and liver and ensure that a necessary amount of a drug, at a desired concentration, reaches the targeted site. Furthermore, growth in treatments involving biologics, which are typically injected in liquid form, has increased the prevalence of parenteral delivery.

Injectable drugs traditionally have been administered via a syringe. Use of a syringe requires insertion of a needle into a patient, and subsequently, driving a plunger through a reservoir to expel a volume of the drug through the needle into the patient. These tasks conventionally have been performed manually. In some situations, it may be necessary or convenient for the patient to self-administer the injectable drug. In the case of a syringe, self-administration requires the patient to manually insert the needle into his or her tissue and then manually advance the plunger. This can be challenging for individuals having limited experience in operating syringes, dexterity problems, a low pain tolerance, among other reasons.

To assist with the self-administration of an injectable drug, various automated drug delivery devices have been developed. One such device is an ambulatory infusion pump used to administer insulin to a diabetic individual. These pumps typically have a processor that follows an internal program to administer a series of doses of insulin to the patient over the course of a day, or several days. Usually the processor is intended for reuse and thus is detachable from other portions of the device, including those which are inserted into the patient. Other automated drug delivery devices, such as certain autoinjectors, are designed to be discarded in their entirety after providing an injection. However, besides providing automatic needle insertion or plunger movement, such disposable devices generally are limited in their ability to assist the patient or user with complying with a prescribed treatment regimen.

The present disclosure sets forth drug delivery systems and related methods of operation embodying advantageous alternatives to existing drug delivery systems and methods of operation, and that may address one or more of the challenges or needs mentioned herein, as well as provide other benefits and advantages.

SUMMARY

One aspect of the present disclosure provides a system for delayed delivery of a drug. The system may include a housing having an interior surface and an exterior surface. The interior surface may define an interior space. The system may include a delivery member configured to have an initial state and a delivery state. In the initial state, the delivery member may be withdrawn inside the interior space of the housing. In the delivery state, a pointed end of the delivery member may extend beyond the exterior surface of the housing for insertion into a patient. The system may also include a reservoir configured to receive a volume of a drug and to be in fluid communication with the delivery member. Additionally, the system may include an energy source activatable by the patient to actuate the reservoir to deliver the volume of the drug to the patient as a single bolus. In addition, the system may include a lockout system configured to have a locked state and an unlocked state. In the locked state, the lockout system may prevent movement of the delivery member relative to the housing and/or activation of the energy source. In the unlocked state, the lockout system may permit movement of the delivery member relative to the housing and/or activation of the energy source. Furthermore, the lockout system may be configured to automatically change from the locked state to the unlocked state after a preselected time period has elapsed.

Another aspect of the present disclosure provides a method of operation of a disposable, single-use injector for drug delivery. The method may comprise: initiating a timer associated with the injector to monitor whether a preselected time period has elapsed; and automatically unlocking a trigger member permitting a patient or a user to activate an energy source of the injector, the energy source being configured to actuate a reservoir to deliver the volume of the drug to a patient as a single bolus via the delivery member upon activation.

An additional aspect of the present disclosure provides a system for delayed delivery of a drug. The system may include a delivery member configured for insertion into a patient, a reservoir configured to receive a volume of the drug and to be in fluid communication with the delivery member, and an actuator configured to expel the volume of the drug from the reservoir to the patient via the delivery member as a single bolus. In addition, the system may include an output element configured to generate a detectable output after at least one condition has been satisfied to notify the patient or a user of the satisfaction of the at least one condition. The at least one condition may comprise a preselected time period. The output element may be configured to generate the detectable output after the timer has determined that the preselected time period has elapsed.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

FIG. 7 is a perspective view of another embodiment of a system including an injector in accordance with principles of the present disclosure.

FIG. 8 is a cross-sectional view taken along line Y-Y in FIG. 7.

DETAILED DESCRIPTION

Figure 1:
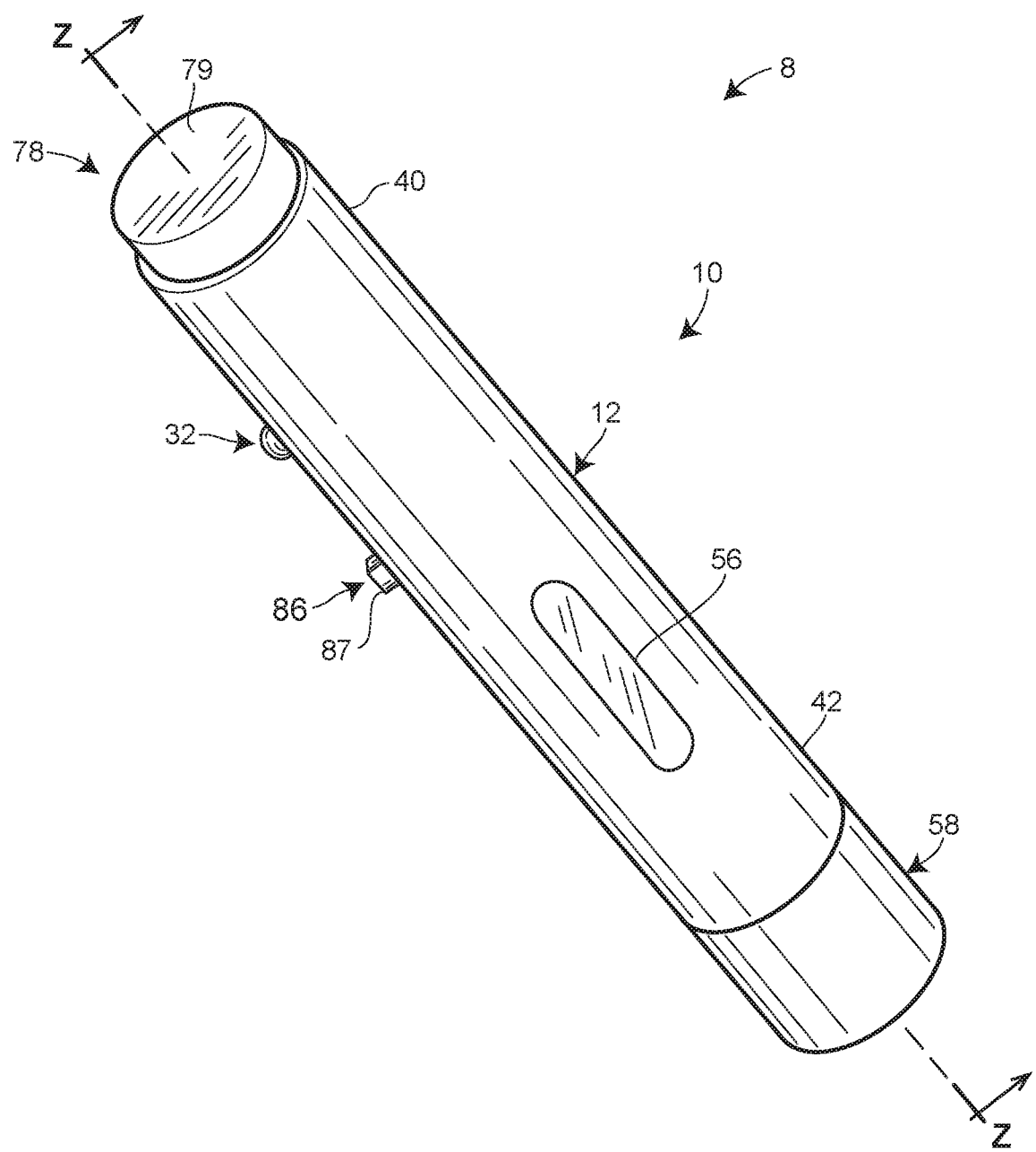
FIG. 1 is an exterior perspective view of an embodiment of a system including an injector in accordance with principles of the present disclosure.

The present disclosure generally relates to systems, devices, and methods facilitating the delayed delivery of a single bolus of an injectable drug. The systems, devices, and methods disclosed herein are particularly well suited for use in addressing an issue for patients undergoing chemotherapy for the treatment of cancer, although they also have uses outside of this particular application.

Chemotherapy agents, such as fludarabine, mitoxantrone, and cyclophosphamide, work in different ways to stop the growth of cancer cells. Some agents act to kill the cancer cells, while other agents work to stop the cancer cells from dividing. At the same time that these chemotherapy agents are working on the cancerous cells, they may have the side effect of suppressing the patient's immune system.

To counter the effects of the chemotherapy agents on the immune system, colony stimulating factors, such as a granulocyte colony stimulating factor (G-CSF), can be administered to increase the number of immune cells (e.g., white blood cells) found in bone marrow or peripheral blood. Studies have shown that the effectiveness of G-CSF depends on the timing of its administration relative to the administration of the chemotherapy agents. G-CSF has been observed to be more effective when administered on the day following the last dose of the chemotherapy agents than if administered simultaneously with or immediately after the chemotherapy treatment. A delay of approximately 24 hours or longer between the last dose of the chemotherapy agents and the administration of the G-CSF has been found to be desirable. As a consequence, unless a patient has the means to self-administer the G-CSF injection, the patient must return to a treatment location, for example the doctor's office, for a separate appointment to receive the injection of G-CSF. This can be inconvenient and undesirable for both the patient and the healthcare provider, particularly if the patient is experiencing acute side effects from the chemotherapy treatment.

To facilitate the self-administration of a G-CSF as well as other injectable drugs requiring or benefiting from a delayed single bolus delivery scheme, the present disclosure describes various automated and semi-automated features for use with an injector. Such features include, but are not limited to, a lockout system for preventing use of the injector until after a preselected time period has elapsed (i.e., passed) and an output element configured to generate a detectable output notifying a patient or user of the injector that the preselected time period has elapsed. Providing such features can aid a patient or user in operating the injector to deliver a single bolus of a drug after a desired waiting period has passed. Accordingly, the chance that the patient or user will administer the drug too soon following a certain medical related event or procedure can be reduced.

FIGS. 1-5 illustrate a system 8 including a hand-held, automated injector 10 for drug delivery, which in certain contexts may be referred to as an autoinjector. The injector 10 may include a housing 12 configured to be held against a patient's skin during drug delivery. As depicted in FIGS. 2-5, a delivery member 14 and a reservoir 16 are disposed within the housing 12, with the delivery member 14 having an initial state wherein a pointed end 18 of the delivery member 14 is withdrawn inside the housing 12 (see FIGS. 2 and 3) and a delivery state wherein the pointed end 18 of the delivery member 14 extends beyond or projects from the housing 12 (see FIGS. 4 and 5). The reservoir 16 may be connected in fluid communication with the delivery member 14 in the delivery state. The injector 10 also includes an energy source 20 which stores energy and is activatable by a patient or user to release the energy to generate a motive force necessary for actuating the reservoir 16 to deliver a volume of a drug 22 contained therein to the patient via the delivery member 14 as a single bolus. In some embodiments, the energy source 20 may also, upon activation by the patient or user, release energy to generate the motive force necessary for moving the delivery member 14 relative to the housing 12 between the initial and delivery states.

The injector 10 may also include a lockout system 30, defined by one or more components, configured to place the injector 10 in a locked state or an unlocked lock. In the locked state, the lockout system 30 may be configured to prevent movement of the delivery member 14 relative to the housing 12 and/or activation of the energy source 20. In the unlocked state, the lockout system 30 may be configured to permit movement of the delivery member 14 relative to the housing 12 and/or activation of the energy source 20. Furthermore, the lockout system 30 may be configured to automatically change from the locked state to the unlocked state after a preselected time period has elapsed. A timer, which may be incorporated into the injector 10 or alternatively exist separately from the injector 10, may be used to determine whether the preselected time period has elapsed. To notify the patient or user of the state of the lockout system 30 or otherwise provide an indication that the time for drug delivery has arrived, the injector 10 may include an output element 32 configured to generate a detectable output (e.g., an audio, visual, tactile, and/or vibrational signal) after the preselected time period has elapsed.

A method of operation of the injector 10 addresses the issue where a single bolus of a drug be delivered at a particular time after a medical event or procedure. At the completion of, or during, such a procedure, the timer associated with the injector 10 may be initiated by most likely, but not exclusively, the patient or individual who is the subject of the medical event or procedure. The timer begins to monitor the elapse or countdown of a preselected time period, with which the timer has been preset by, for example, a manufacturer of the injector 10. After the preselected time period is determined to have elapsed, the lockout system 30 may automatically switch the injector 10 from the locked state, which may have been established at the time of manufacturing, to the unlocked state in order to permit use of the injector 10 by the patient or user for drug delivery. Also, after the preselected time period has elapsed, the output element may generate a detectable output to notify the patient or user that the injector 10 is now operable for drug delivery.

As a consequence of the use of such an injector 10, the patient may not be required to return to the healthcare provider for the purpose of receiving a single injection of a drug. This has benefits for the patient, in that the patient can focus on the healing process without the burden of having to make a return trip to the healthcare provider. The healthcare provider also benefits in that they can rely on the patient to self-administer the injection with at least some assurance as to the issue of timing. This, in turn, frees resources that would be tasked for the patient's return visit to instead be used for the healthcare of other patients.

Having described the injector 10 and its use in general terms, the structure and operation of the injector 10 is now described in greater detail. FIG. 1 is a perspective view of one embodiment of the injector 10. The injector 10 may be configured as a single-use disposable injector, or as a reusable injector. The injector 10 may be configured for self-administration by the patient, although in some versions could also be used by a caregiver or other healthcare provider to administer an injection.

Referring to FIGS. 2-5, the housing 12 may be sized and dimensioned to enable a person to grasp the injector 10 in a single one of his or her hands. In some embodiments, the housing 12 may be disposable and/or made of a plastic material. The housing 12 may have a generally elongate shape, such as a cylinder, extending along a longitudinal axis A1 between a proximal end 40 and a distal end 42. An opening 44 may be formed in the distal end 42 to permit the delivery member 14 to be deployed from the housing 12 during use.

The housing 12 may be a single, unitary component, or, as seen in FIGS. 2-5, defined by multiple interconnected components. FIGS. 2-5 illustrate that the proximal end 40 is defined by an outer sleeve 46 and that the distal end 42 is defined by an inner sleeve 48. The inner sleeve 48 may be slidably disposed within the outer sleeve 46 to provide a deployable guard member for preventing inadvertent contact with the pointed end 18 of the delivery member 14 before and/or after drug delivery.

Figure 2:
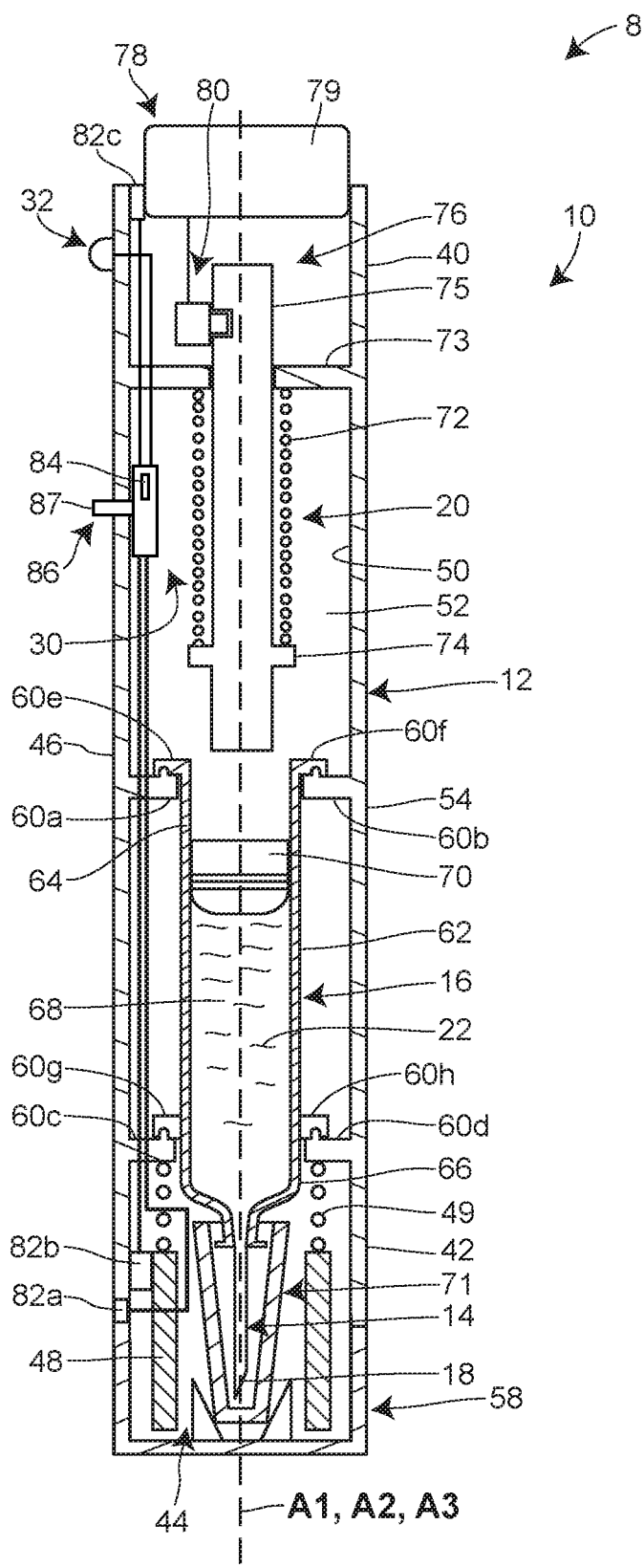
FIG. 2 is a schematic cross-sectional view of the injector depicted in FIG. 1 taken along line Z-Z.
Figure 3:
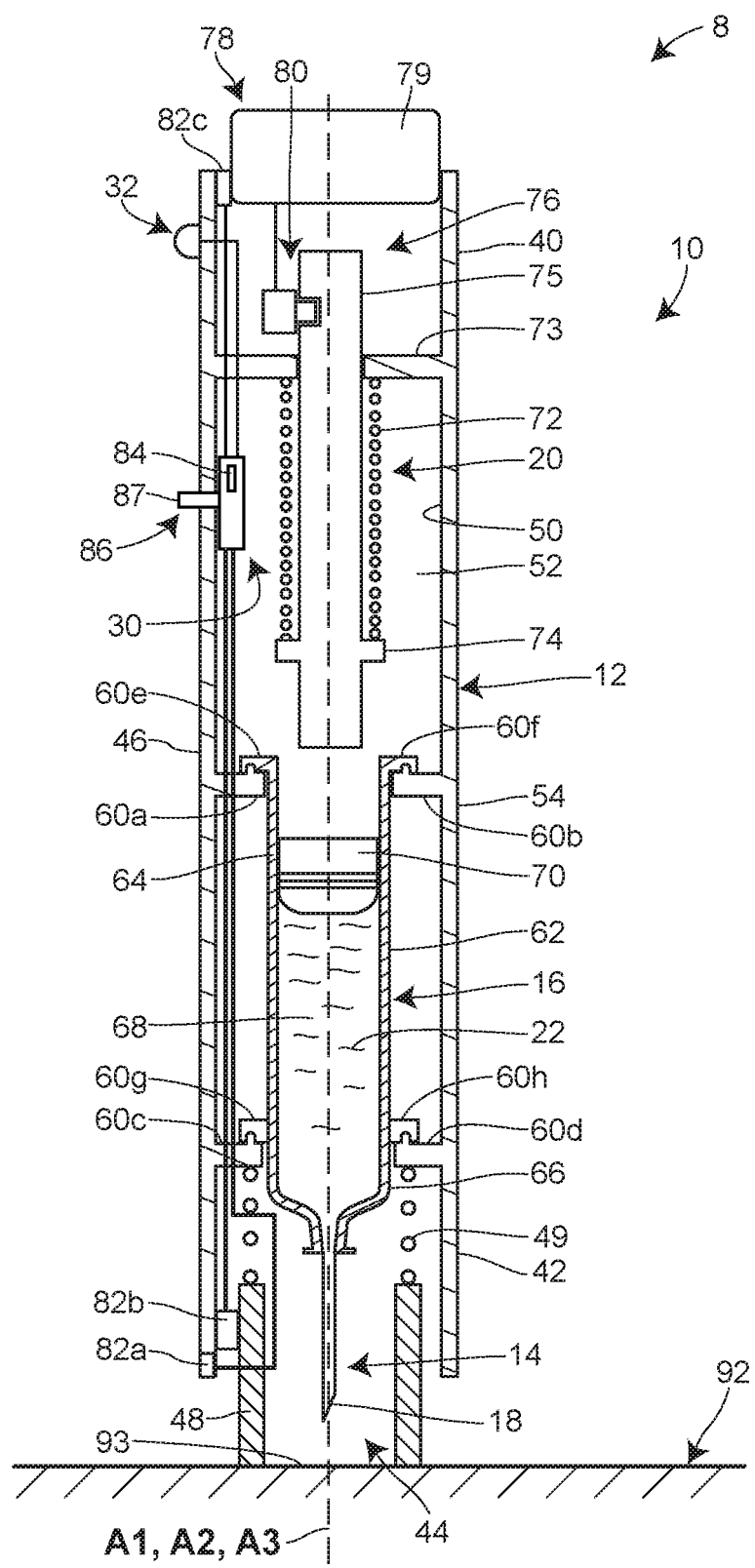
FIGS. 3-5 illustrate a sequence of steps for using the injector depicted in FIG. 2 to deliver a volume of a drug to a patient as a single bolus, in accordance with an embodiment of the present disclosure.
Figure 4:
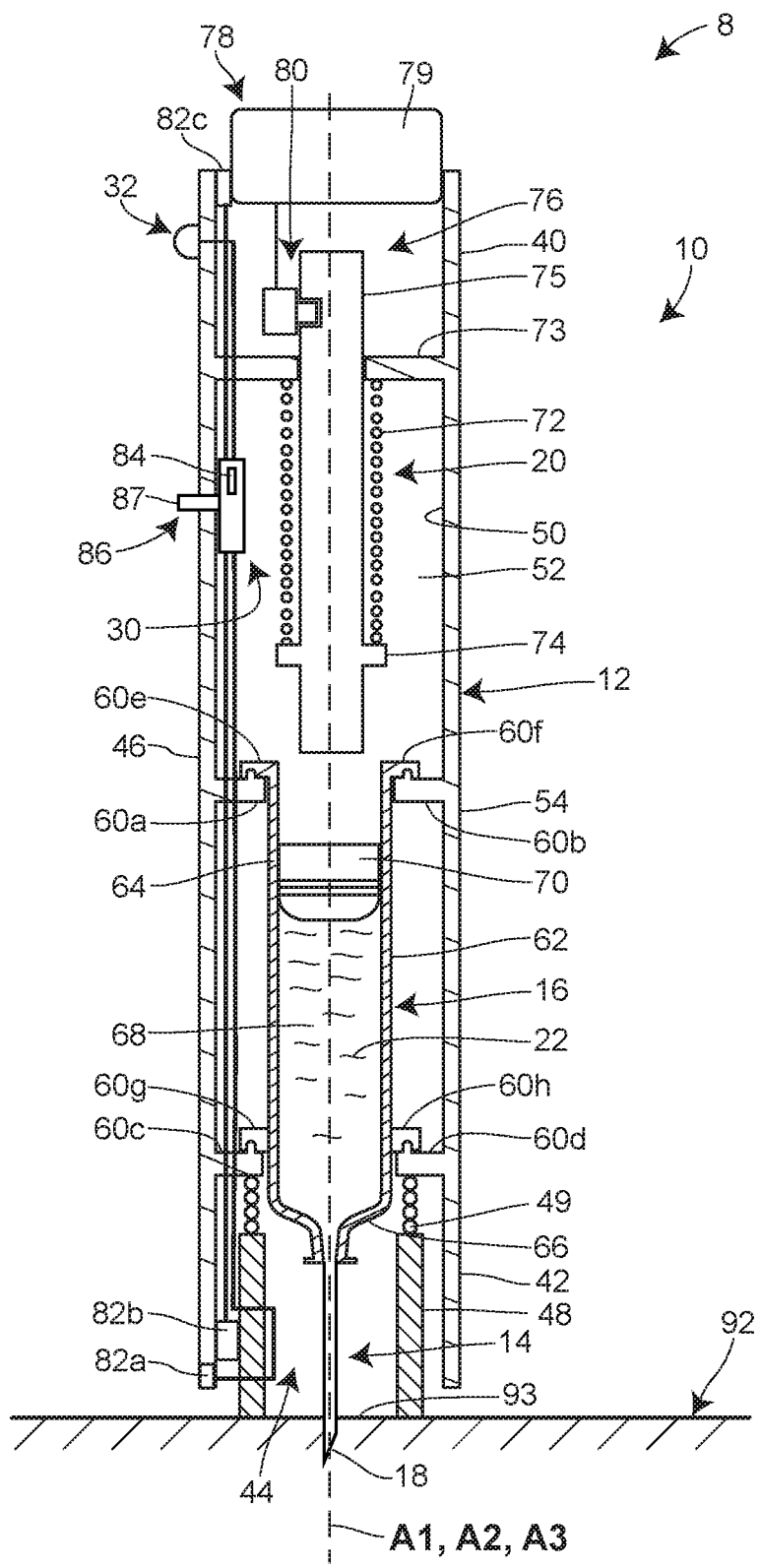

The housing 12 may have an interior surface 50 defining an interior space 52 and an exterior surface 54. When the inner sleeve 48 is arranged in its deployed position as seen FIG. 3, the exterior surface 54 of the housing 12 may be defined by an exterior surface of the outer sleeve 46 and an exterior surface of the inner sleeve 48. When the inner sleeve 48 is arranged in its retracted position as shown in FIG. 4, the exterior surface 54 of the housing 12 may be defined only by the exterior surface of the outer sleeve 46. As shown in FIGS. 2 and 3, a biasing member 49 such as a spring may be included for urging the inner sleeve 48 toward the deployed position. A biasing force generated by the biasing member 49 may be overcome by pressing the inner sleeve 48 against the patient's skin.

As seen in FIG. 1, a transparent or semi-transparent inspection window 56 may be positioned in a wall of the housing 12 to permit the patient or user to view the reservoir 16 and/or the drug 22 contained therein. The inspection window 56 may be formed in the outer sleeve 46 of the housing 12 in some versions. The inspection window 56 may permit visual inspection for any one or more of the following reasons: for assurance that the injector 10 has been filled or filled with a proper amount of the drug 22 prior to activation of the injector 10; for inspection of the drug 22 to ensure quality; and for confirmation that the drug 22 is being/has been delivered to the patient.

As seen in FIGS. 1 and 2, a removable cap 58 initially may cover the opening 44 formed in the distal end 42 of the housing 12. Prior to operation of the injector 10, a patient or user may remove the removable cap 58 from the housing 12 to uncover the opening 44, thereby allowing the delivery member 14 to be deployed from the housing 12. The connection between the removable cap 58 and the housing 12 may, in some embodiments, be provided by a friction or snap fit connection, a frangible or breakaway connection, and/or an interlocking arrangement. Furthermore, in some embodiments, the removable cap 58 may seal the interior space 52 of the housing 12 prior to its removal.

As noted above, the drug 22 may be contained within a reservoir 16 that is disposed within the interior space 52 of the housing 12. The reservoir 16 may be pre-filled with a volume of the drug 22 by a manufacturer, for example, or, alternatively, filled with a volume of the drug 22 at the time of treatment by the patient or user. In such alternative embodiments, the injector 10 may include a fill port having an inlet disposed in the exterior surface 54 of the housing 12 and in selective fluid communication with the reservoir 16 in order to permit the patient or user to fill the reservoir 16 with a drug from an external source.

In some embodiments, the reservoir 16 may be a conventional syringe having a staked needle configured as the delivery member 14; whereas, in other embodiments, the reservoir 16 may be a needle-less cartridge having a septum which is pierced otherwise accessed by a proximal end of the delivery member 14 during operation or initiation of the injector 10. Furthermore, the reservoir 16 may be pre-loaded or otherwise pre-installed within the housing 12 by, for example, a device manufacturer. Alternatively, the reservoir 16 may be installed within the housing 12 at the time of treatment by the patient or user. In embodiments where the injector 10 is designed to be reusable, the reservoir 16 may be removed from the housing 12 after the completion of drug delivery and replaced with a new reservoir. A wall of the reservoir 16 may be made of glass or plastic.

As seen in FIGS. 2-5, the longitudinal axis A1 of the housing 12, a longitudinal axis A2 of the delivery member 14, and/or a longitudinal axis A3 of the reservoir 16 may be parallel or otherwise non-perpendicular to each other. Moreover, any one or combination of the longitudinal axes A1, A2, and A3 may be coaxial with each other. A parallel alignment of axes A1, A2, and A3 can result an elongate overall shape of the injector 10, which can be held with ease in the hand of the patient or user.

In the embodiment shown in FIGS. 2-5, the reservoir 16 is fixedly connected to the housing 12 via a plurality of interlocking mounting structures 60*a-h* such that the reservoir 16 cannot translate or rotate relative to the housing 12. In alternative embodiments, the reservoir 16 may be movably connected to the housing 12 via a carrier assembly, for example, such that the reservoir 16 translates in a distal direction and/or proximal direction relative to the housing 12 along the longitudinal axis A1 during operation of the injector 10. In such alternative embodiments, distal movement of the reservoir 16 may cause the delivery member 14 to transition from the initial state, wherein the pointed end 18 of the delivery member 14 is withdrawn inside the interior space 52 of the housing 12, to the delivery state, wherein the pointed end 18 of the delivery member 14 extends beyond the exterior surface 54 of the housing 12.

Still referring to FIGS. 2-5, the reservoir 16 may be defined by a hollow, rigid-walled cylinder 62 having a proximal end 64 and a distal end 66. The delivery member 14 may be fixedly connected to the distal end 64 of the reservoir 16. An interior space or bore 68 of the reservoir 16 may be configured to receive a volume of the drug 22. According to certain embodiments, the drug 22 may be a G-CSF, a pegylated G-CSF, or any other desired pharmaceutical. For example, the pharmaceutical may be an erythropoiesis stimulating agent, a TNF blocker, interleukin receptor specific antibodies, IGF-receptor specific antibodies, or TGF-specific antibodies. Moreover, the drug 22 may be any one of or any combination of the drugs listed below under the heading "Drug Information."

In addition to the volume of the drug 22, a stopper or plunger 70 may be also be disposed in the interior space 68 of the reservoir 16. The stopper 70 may slidably and sealably engage an interior surface of the reservoir 16. During drug delivery, movement of the stopper 70 in the distal direction along the longitudinal axis A3 may cause the volume of the drug 22 to be expelled from the reservoir 16 and into the delivery member 14 such that the two elements are in fluid communication with each other. As seen in FIGS. 2-5, the proximal end 64 of the reservoir 16 may be open to allow a plunger to extend into the interior space 68 of the reservoir 16 to push the stopper 70 in the distal direction.

According to other variants, a non-rigid collapsible pouch may be substituted for the rigid-walled cylinder 62 and the stopper 70. In such variants, a spring-based mechanical system, gas-generating system, or other system may be used to compress the pouch in order to expel the volume of the drug contained therein.

As noted above, the delivery member 14 may have a pointed end 18. One or more openings may be formed in and/or near the pointed end 18 to permit the drug 22 to be expelled from the reservoir 16 and delivered to the patient, for example, subcutaneously. The delivery member 14 may have an initial or storage state wherein the pointed end 18 of the delivery member 14 is withdrawn inside the interior space 52 defined by the housing 12 (see FIGS. 2 and 3). The deliver member 14 may also have a deployed or delivery state wherein the pointed end 18 of the delivery member 14 projects from the interior space 52 beyond the exterior surface 54 of the housing 12 (see FIGS. 4 and 5). In the embodiment illustrated in FIGS. 2-5, the initial state of the delivery member 14 is defined by the inner sleeve 48 arranged in a deployed position where it extends from the outer sleeve 46 to cover the pointed end 18 of the delivery member 14. The delivery state of the delivery member 14 is defined by the inner sleeve 48 being retracted within the outer sleeve 46 to expose the pointed end 18 of the delivery member 14. Also, in the present embodiment, the delivery member 14 remains stationary relative to the proximal end 40 of the housing 12 as it transitions from the initial state to the delivery state. However, the present disclosure is not limited to this configuration; alternative embodiments may involve the delivery member 14 moving away from the proximal end 40 of the housing 12 as the delivery member 14 transitions from the initial state to the delivery state.

In the embodiment shown FIGS. 2-5, the delivery member 14 is configured as a rigid, hollow needle. In alternative embodiments, such as the wearable version of the injector described below, the delivery member 14 may be formed by the combination of a soft cannula and a rigid needle, the latter of which may be solid or hollow. In such alternative embodiments, the rigid needle may be used to initially pierce the patient's tissue to form an entry path for introducing the soft cannula. This introducing function of the rigid needle may be facilitated by constructing the rigid needle of a more rigid material than the soft cannula. For instance, the rigid needle may be made of metal, whereas the soft cannula may be made of plastic. In certain embodiments, the soft cannula may have a blunt tip.

The pointed end 18 of the delivery member 14 may be sharp enough to penetrate at least through the epidermis and dermis and into the subcutaneous tissue.

As illustrated in FIG. 2, a removable shield 71 (e.g., a rigid needle shield) may be installed over the pointed end 18 of the delivery member 14 for maintaining sterility of the delivery member 14 prior to use of the injector 10. In some embodiments, removal of the removable cap 58 may simultaneously detach the removable shield 71 from the delivery member 14. This may be accomplished by configuring an interior surface of the removable cap 58 to frictionally grip the exterior surface of the removable shield 71.

With continued reference to FIGS. 2-5, the energy source 20 may be connected to and disposed within the interior space 52 of the housing 12. In general terms, the energy source 20 provides the energy needed for expelling the volume of the drug 22 contained in the reservoir 16. The energy source 20 may also, in certain embodiments, provide the energy needed for moving the delivery member 14 relative to the housing 12 between the initial state and the delivery state and/or powering other automated features including electronic features. The energy source 20 may be configured to store mechanical, electrical, and/or chemical energy prior to activation. Upon activation, the energy source 20 may release or otherwise output this energy in order to generate the motive force(s) needed for actuating one or more components of the injector 10. The energy source 20 may take any form including, but not limited to, one or more springs (e.g., a helical compression spring, a helical extension spring, a helical torsion spring, a spiral torsion spring, etc.), one or more batteries, and/or one or more gas- or liquid-generating chemicals. In the embodiment illustrated in FIGS. 2-5, the energy source 20 is defined by a helical compression spring 72 initially retained in a compressed or energized state between an inwardly-extending flange 73 fixedly connected to the housing 12 and an outwardly-extending flange 74 fixedly connected to a plunger rod 75. Activation of the spring 72 involves releasing the spring 27 so that it can expand in length to a de-energized state.

In embodiments where the injector 10 is configured for single-use and disposal immediately thereafter, the energy source 20 may be configured to output most or all of its stored energy in a single action, or a single sequence of actions, upon activation of the energy source 20. Moreover, in such embodiments the energy source 20 may be configured such that the patient or user is prevented from re-energizing the energy source 20 after the energy source 20 has been activated. This aspect of the energy source 20 may be facilitated by enclosing the energy source 20 within the interior space 52 of the housing 12.

In embodiments where the injector 10 is configured for single-use and disposal immediately thereafter, the energy source 20 may be configured to be activated only once. In some such embodiments, the energy source may be configured to undergo an irreversible process, or at least a process that is irreversible by the patient or user of the injector 10, by releasing its stored energy.

As noted above, the energy source 20 provides the energy needed at least for expelling the volume of the drug 22 contained in the reservoir 16. Furthermore, the energy source 20 may be configured such that, upon activation, the energy source 20 outputs a sufficient amount of energy for expelling the entire volume, or substantially all of the volume, of the drug 22 contained in the reservoir 16 all at once to the patient as a single bolus. This may involve the energy source 20 releasing enough energy to drive the stopper 70 in a single continuous motion from an initial position near the proximal end 64 of the reservoir 16 (see FIG. 4) to a final position near the distal end 66 of the reservoir 16 where the stopper 70 contacts a proximally-facing interior surface of the reservoir 16 (see FIG. 5). At least in embodiments where the injector 10 is held in the patient's hand over the course of drug delivery, the rate at which the energy source 20 outputs its stored energy upon activation may be sufficient for expelling the entire volume, or substantially all of the volume, of the drug 22 contained in the reservoir 16 as single bolus to the patient in a time period less than approximately (e.g., ±10%) 30 seconds, or less than approximately (e.g., ±10%) 20 seconds, or less than approximately (e.g., ±10%) 15 seconds, or less than approximately (e.g., ±10%) 10 seconds, or less than approximately (e.g., ±10%) 6 seconds, or in a range between approximately (e.g., ±10%) 5-30 seconds, or in a range between approximately (e.g., ±10%) 5-15 seconds. In embodiments where the injector 10 is attached to or worn on the patient's skin (e.g., via an adhesive) over the course of drug delivery, the rate at which the energy source 20 outputs its stored energy upon activation may be sufficient for expelling the entire volume, or substantially all of the volume, of the drug 22 contained in the reservoir 16 as single bolus to the patient in a time period greater than approximately (e.g., ±10%) 10 minutes, or in a range between approximately (e.g., ±10%) 10-60 minutes, or shorter time periods such as any of those described in the preceding sentence.

An actuator 76 may be included within the housing 12 for converting or directing the energy output by activation of the energy source 20 into movement of one or more components of the injector 10. In the embodiment illustrated in FIGS. 2-5, the actuator 76 takes the form of a plunger rod 75 which directs the mechanical energy released by the spring 72 into distal movement of the stopper 70 through the reservoir 16. The actuator 76 is not limited to a plunger and may additionally, or alternatively, include an electric motor, a gear train, one or more telescopically arranged sleeves, a hydraulically or pneumatically-driven piston element, and/or any other mechanism or electromechanical feature suitable for transforming the energy stored by the energy source 20 into useful mechanical work. In embodiments where the actuator 76 is an electric motor, for example, the actuator 76 may convert one type of energy (e.g., electrical energy) into a another type of energy (e.g., mechanical energy). Also, it should be noted that the energy source 20 and the actuator 76 can be the same component in certain embodiments, such as an embodiment where the energy source 20 is a spring which bears directly upon the stopper 70.

Another aspect of the energy source 20 is that it may be configured for activation by a patient at the time of drug delivery. The energy source 20 may begin outputting its stored energy simultaneously with, or immediately after, activation of the energy source 20 by the patient. As a consequence, the patient may begin to receive an injection of the drug 22 immediately after activation of the energy source 20, or within a few seconds or tens of seconds thereof.

Activation of the energy source 20 by the patient may be accomplished through a variety of different mechanical, electromechanical, and/or electrical features. In some embodiments, activation of the energy source 20 is achieved by the patient manually applying a force to a trigger member 78 in order to move the trigger member 78 relative to a portion of the injector 10. Movement of the trigger member 78 may cause the trigger member 78 through a mechanical or electromechanical connection with the energy source 20 to interact with and activate the energy source 20. In the embodiment illustrated in FIGS. 1-5, the trigger member 78 is a button 79 which protrudes through an opening formed in the proximal end 40 of the housing 12 and which is manually depressible into the housing 12 in a distal linear direction. Depressing the button 79 into the housing 12 causes the button 79 to mechanically interact with a plunger retaining mechanism 80, thereby transforming the plunger retaining mechanism 80 from a retaining configuration, wherein the plunger retaining mechanism 80 interlocks with the plunger rod 75 to prevent the plunger rod 75 from moving in the distal direction via expansion of the spring 72 (see FIGS. 2-4), to a releasing configuration, wherein the plunger retaining mechanism 80 disengages from the plunger rod 75 to permit distal movement of the plunger rod 75 via expansion of the spring 72 (see FIG. 5). Accordingly, depression of the button 79 into the housing 12 activates the energy source 20 by removing any barriers to expansion of the spring 72. In alternative embodiments, manually depressing the button 79 may complete or activate an electrical circuit, which in turn may result in the transmission of an electrical signal for activating a battery-type energy source 20.

In further alternative embodiments, the button 79 may be omitted and instead the inner sleeve 48 may function as the trigger member 78. Here, retraction of the inner sleeve 48 into the outer sleeve 46, which results in the delivery member 14 transitioning from its initial state to its delivery state, may also cause the inner sleeve 48 through a mechanical or electromechanical connection with the energy source 20 to interact with and activate the energy source 20.

As mentioned above, certain aspects of the operation of the injector 10 may be controlled by a lockout system 30. Generally, the lockout system 30 is intended to inhibit or prevent premature use of the injector 10 by the patient or user. More particularly, the lockout system 30 inhibits or prevents the patient or user from using the injector 10 to administer the drug 22 until after a preselected time period has elapsed. The lockout system 30 may be configured to have a locked state, wherein the lockout system 30 prevents movement of the delivery member 14 relative to the housing 12 and/or activation of the energy source 20, and an unlocked state, wherein the lockout system permits movement of the delivery member 14 relative to the housing 12 and/or activation of the energy source 20. Furthermore, the lockout system 30 may be configured to automatically change from the locked state to the unlocked state after a preselected time period has elapsed. Accordingly, the patient may be unable to inject himself with the delivery member 14 and/or expel the drug 22 from the reservoir 16 until lockout system 30 has determined that the preselected time period has elapsed and placed the injector 10 in the unlocked state. The lockout system 30 advantageously allows the healthcare provider to rely on the patient to self-administer the drug 22 with at least some certainty that the drug 22 will be delivered in accordance with a desired delay. The lockout system 10 may be implemented via a mechanical device, a combination of mechanical devices, an electrical device (e.g., a hardwired circuit or a programmable controller), a combination of electrical devices, a chemical device, a combination of chemical devices, or any combination thereof (e.g., an electromechanical device, an electrochemical device, etc.).

In embodiments where the injector 10 is configured for single-use and disposal thereafter, the lockout system 30 may be configured to change from the locked state to the unlocked state only once. In some such embodiments, the lockout system 30 may be configured to undergo an irreversible process, or at least a process that is irreversible by the patient or user of the injector 10, when changing from locked state to the unlocked state.

In some embodiments, the lockout system 30 may be configured in the locked state by a device manufacturer. This may require the device manufacturer to configure the lockout system 30 in the locked state prior to disposing, and optionally sealing, the lockout system 30 within the housing 12 of the injector 10. As a result, the injector 10 may already be configured in the lockout state when obtained by the patient or healthcare provider. In alternative embodiments, the patient or healthcare provider may be relied upon for initially placing the lockout system 30 in the locked state.

The lockout system 30 may include one or more resistance units configured to selectively resist movement of one or more components of the injector 10. In the embodiment illustrated in FIGS. 2-5, the injector 10 includes a resistance unit 82a for selectively resisting movement of the removable cap 58, a resistance unit 82b for selectively resisting movement of the inner sleeve 48, and a resistance unit 82c for selectively resisting movement of the trigger member 78. In alternative embodiments, the injector 10 may incorporate only one or some of the resistance units 82a-c and/or additional resistance unit(s). Furthermore, in certain embodiments where a programmable controller is configured for controlling the actuation of some or all of the moveable components of the injector 10, the injector 10 may not include any resistance units and instead rely on the software or other programming of the controller to implement the locked and/or unlocked states. Such a controller, in the locked state, may be programmed to not operate an electric motor, for example, in response to commands from a patient or user to deploy the delivery member 14 and/or active the energy source 20.

In some embodiments, one or more of the resistance units 82a-c may be configured as an electromechanical lock, or as a solely mechanical lock having a time delay aspect. In the electromechanical lock, each of the resistance units 82a-c may include a solenoid, magnet, or electric motor which is responsive to an electrical signal for engaging or disengaging a pin, latch, plate, or other moveable locking member. In alternative embodiments, one or more of the resistance units 82a-c may be configured to implement an unlocked or locked state via a controlled chemical reaction.

The resistance unit 82a may be fixedly connected, directly or indirectly, to one of the housing 12 and the removable cap 58 and selectively mechanically engaged with the other one of the housing 12 and the removable cap 58. When the resistance unit 82a is mechanically engaged with the other one of the housing 12 and the removable cap 58, the resistance unit 82a may be configured to resist removal of the removable cap 58 from the housing 12 and thereby define the locked state. When the resistance unit 82a is mechanically disengaged from the other one of the housing 12 and the removable cap 58, the resistance unit 82a may not be configured to resist removal of the removable cap 58 from the housing 12 and thus define the unlocked state.

The resistance unit 82b may be fixedly connected to, directly or indirectly, to one of the outer sleeve 46 and the inner sleeve 48 and selectively mechanically engaged with the other one of the outer sleeve 46 and the inner sleeve 48. When the resistance unit 82b is mechanically engaged with the other one of the outer sleeve 46 and the inner sleeve 48, the resistance unit 82b may be configured to resist retracting and/or deploying movement of the inner sleeve 48 relative to the outer sleeve 46 and thereby define the locked state. When the resistance unit 82b is mechanically disengaged from the other one of the outer sleeve 46 and the inner sleeve 48, the resistance unit 82b may not be configured to resist retracting and/or deploying movement of the inner sleeve 48 relative to the outer sleeve 46 and thus define the unlocked state.

The resistance unit 82c may be fixedly connected, directly or indirectly, to one of the housing 12 and the trigger member 78 (e.g., the button 79) and selectively mechanically engaged with the other one of the housing 12 and the trigger member 78. When the resistance unit 82c is mechanically engaged with the other one of the housing 12 and the trigger member 78 and to define the locked state, the resistance unit 82c may be configured to resist triggering movement or any other movement of the trigger member 78 relative to the housing 12. When the resistance unit 82c is mechanically disengaged from the other one of the housing 12 and the trigger member 78, the resistance unit 82c may not be configured to resist movement of the trigger member 78 relative to the housing 12 and thus define the unlocked state.

In some embodiments, the resistance units 82a-c may be individually operable such that each can be separately operated to resist or permit movement of its respective injector component. In other embodiments, the resistance units 82a-c may be operated in unison.

As noted above, the lockout system 30 may include a timer 84 for determining whether a preselected time period has elapsed. At the end of a duration of the preselected time period, the timer 84 may output a timer expiration signal (e.g., a mechanical, electrical, electromagnetic, or chemical signal) which causes the lockout system 30 to automatically change from the locked state to the unlocked state and/or causes the output element 32 to generate a detectable output. In some embodiments, the lockout system 30 may automatically change from the locked state to the unlocked state immediately upon receipt of the timer expiration signal. In some embodiments, the timer expiration signal which is output by the timer 30 after the elapse of the preselected time period may directly or indirectly cause one or more of the resistance units 82*a-c* to permit movement of one or more of the removable cap 58, the inner sleeve 48, and the trigger member 78.

The timer 84 may be a mechanical device, a combination of mechanical devices, an electrical device (e.g., a hardwired circuit or a programmable controller), a combination of electrical devices, a chemical device, a combination of chemical devices, or any combination thereof (e.g., an electromechanical device, an electrochemical device, etc.). In some embodiments, the timer 84 may be a set of non-transitory computer-executable instructions programmed into a memory device disposed within or outside of the interior space 52 of the housing 12.

Once initiated, the timer 84 may begin to monitor whether the preselected time period has elapsed. The timer 84 may be configured to perform this action by accessing a hardwired timer circuit or a timer program stored in a memory device. Alternatively, in a mechanical implementation of the timer 84, the timer 84 may utilize one or more of the following for determining whether the preselected time period has elapsed: a clockwork mechanism, a spring-driven mechanism (a mechanism driven by, e.g., a helical compression spring, a helical extension spring, a helical torsion spring, a spiral torsion spring, etc.), a dashpot timer, or any combination thereof. One benefit of the use of a mechanical timer is the elimination of batteries, making the injector 10 potentially less costly and/or more environmentally friendly for the purposes of disposal. In an embodiment where the timer 84 utilizes a spring, the spring may be configured to have an energized state (e.g., a compressed state) at the beginning of the preselected time period and a de-energize state (e.g., an expanded state) at the end of the preselected time period. In still further alternative embodiments, the timer 84 may utilize a chemical substance(s) which, upon being initiated, begins to undergo a chemical reaction at a predicted or expected rate, with the chemical reaction finishing upon the expiration of the preselected time period. Such a chemical reaction may increase a volume of a hollow component by generating a gas or liquid, or may change the electrical conductivity of a component used in an electrical circuit.

In some embodiments, the timer 84 may be built into the injector 10 and disposed within the interior space 52 of the housing 12. In alternative embodiments, the timer 84 may be disposed outside of the housing 12 and part of a standalone device separate from the injector 10. In such alternative embodiments, the timer 84 may transmit the timer expiration signal to the injector 10 via wireless communications. Additionally or alternatively, the timer 84 may be incorporated into the protective disposable packaging within which the injector 10 is shipped or stored by a manufacturer or supplier and which is removed by the patient or user prior to use of the injector 10.

In some embodiments, the timer 84 may be set, programmed, or otherwise configured with the preselected time period by a manufacturer such that the patient or user of the injector 10 is not required to choose a length of time for the preselected time period. In this way, the injector 10, or at least the timer 10, may be received by the patient or user in a ready-to-use format. The length or duration of the preselected time period may be chosen by the manufacturer depending upon the circumstances of the particular application. In some embodiments, the timer 84 may be configured with the preselected time period before the timer 84 is disposed, and optionally sealed, within the interior space 52 of the housing 12. Thus, once the timer 84 is disposed in the interior space 52 and the housing 12 is closed (and potentially sealed), the timer 84 may not be reconfigured with respect to the length of the preselected time period. Nonetheless, the patient or user may still be able to initiate the timer 84 to begin monitoring whether the preselected time period has elapsed.

In alternative embodiments, the timer 84 may include a time selector element permitting the patient or user to set or adjust the length of the preselected time period. In a mechanical version of the timer 84, such a time selector element may enable the patient or user to store the timer 84 with mechanical energy via winding or button pushing in order to set the length of the preselected time period. In an electrical version of the timer 84, the time selector element may permit the patient or user to digitally input the desired length of the preselected time period.

In embodiments where the injector 10 is configured for single-use and disposal immediately thereafter, the timer 84 may be configured to determine whether any preselected time period has elapsed only once. In some such embodiments, the timer 84 may be configured to undergo an irreversible process, or at least a process that is irreversible by the patient or user of the injector 10, by determining whether the preselected time period has elapsed.

As mentioned above, the length of the preselected time period may depend on the particular application and/or formulation of the drug 22 included in the reservoir 16. In embodiments where the injector 10 is intended to deliver a G-CSF following a chemotherapy treatment, the length of the preselected time period may be chosen as any duration within a range between approximately (e.g., ±10%) 24-27 hours, such as 24, 25, 26, or 27 hours or fractions thereof, such as 24.5 hours. Alternatively, the length of the preselected time period may be chosen as any duration within a range between approximately (e.g., ±10%) 22-29 hours, such as 22, 23, 24, 25, 26, 27, 28, 29 hours or fractions thereof, such as 22.5 hours. As a still further alternative, the length of the preselected time period may be chosen as any duration longer than approximately (e.g., ±10%) 24 hours, such as 27, 30, 33, 36, or 48 hours or fractions thereof, such as 27.5 hours. As a still further alternative, the length of the preselected time period may be chosen as any duration longer than approximately (e.g., ±10%) 18 hours, such as 20, 21, 31, or 32 hours or fractions thereof, such as 20.1 hours. In still further alternatives, the length of the preselected time period may be chosen as a duration lying outside the previously recited ranges.

An initiator 86 may be included to enable the patient or other user of the injector 10 to initiate the operation of the timer 84 so that it begins to monitor the elapse of the preselected time period, or otherwise operates according to its configuration or programming. The initiator 86 may be connected to and/or in communication with (e.g., via wired or wireless communications) with the timer 84. In some embodiments, the initiator 86 permit the patient or user of the injector 10 to initiate operation of the timer 84 without permitting the patient or user to adjust a length of the preselected time period. In such embodiments, the sole function of the initiator 86 may be to initiate the countdown by the timer 84. Furthermore, in such embodiments, neither the initiator 86 nor any other portion of the injector 10 may permit the user or patient to adjust a length of the preselected time period. Furthermore, in some embodiments, such as those where the injector 10 is configured for single-use and disposal immediately thereafter, the initiator 86 may be configured to initiate the timer 84 only once. In one such embodiment, the initiator 86 may be configured as a depressible button, and the button may remain depressed into a recess after being pushed on by the patient or user, thereby preventing the user or patient from depressing the button into the recess a second or further time. Accordingly, the initiator 86 may be configured to undergo an irreversible process, or at least a process that is irreversible by the patient or user of the injector 10, when initiating the timer 86.

The initiator 86 may be a mechanical device, a combination of mechanical devices, an electrical device (e.g., a hardwired circuit or a programmable controller), a combination of electrical devices, a chemical device, a combination of chemical devices, or any combination thereof (e.g., an electromechanical device, an electrochemical device, etc.). In some embodiments, the initiator 86 may be configured to initiate the timer 84 upon application of a force by the patient or user. In such embodiments, the manual application of the force moves the initiator 86, which in turn initiates the timer 84 through a mechanical and/or electromechanical connection existing between the initiator 86 and the timer 84. In some embodiments, the initiator 86 may be slidably or rotatably connected to the housing 12. In the embodiment illustrated in FIGS. 1-5, the initiator 86 is a button 87 which protrudes outwardly through an opening formed in the exterior surface 54 of the housing 12 and which is manually depressible into the housing 12. At least a portion of the initiator 86 may be disposed outwardly of or flush with the exterior surface 54 of the housing 12. Alternatively, the initiator 86 may be defined by a portion of the exterior surface 54 of the housing 12. In further alternative embodiments, the initiator 86 may be recessed within the housing 12, such that a tool or instrument (e.g., a pin, key, or needle) must be disposed into or through an opening formed in the exterior surface 54 of the housing 12 to initiate the timer 84. In still further alternative embodiments, the initiator 86 may disposed within the interior space 52 of the housing 12 and actuated by installation of the reservoir 16 within the interior space 52 of the housing 12 by the patient or user. In still further alternative embodiments, the initiator 86 may be a touchscreen or electrical switch built into the injector 10 and operable by the patient or user through touch.

In still further alternative embodiments, the initiator 86 may be detachably connected (e.g., via a frangible or breakaway connection) to an element that is removed from the injector 10 by the patient or user prior to drug delivery. Removal of the element from the injector 10 by the patient or user may cause movement of the initiator 86, which in turn may initiate operation of the timer 84. Examples of such a removable element include the removable cap 58, or the protective disposable packaging in which the injector 10 is shipped or stored by a manufacturer or supplier and which is removed by the patient or user prior to use of the injector 10.

While each of the foregoing embodiments of the initiator 86 requires manual application of a force by the patient or user, alternative embodiments of the initiator 86 may be configured to initiate the timer 84 in response to receiving an electric or electromagnetic signal. In one such alternative embodiment, the initiator 86 may initiate the timer 84 in response to a wireless control signal received from an external or mobile computing device such as a smartphone.

In addition to initiating the timer 84, the initiator 84 may also be configured to place the lockout system 30 in the locked state in some embodiments. Thus, by actuating or otherwise interacting with the initiator 84, the patient or user may simultaneously initiate the countdown by the timer 84 and place the lockout system 30 in the locked state.

As noted above, the system 8 may include an output element 32 for automatically notifying the patient or other user of the injector 10 of relevant information. The output element 32 may be configured to generate a detectable output after one or more conditions has been satisfied in order to notify the patient or user of the satisfaction of the one or more conditions. The one or more conditions may include the expiration of the preselected time period describe above. Accordingly, the output element 32 may be configured to generate the detectable output after the timer 86 has determined that the preselected time period has elapsed. In some embodiments, the output element 32 may generate the detectable output in response to or upon receipt of the timer expiration signal (e.g., a mechanical, electric, electromagnetic, or chemical signal) output by the timer 84 at the end of the duration of the preselected time period. In some embodiments, the output element 32 may generate the detectable output simultaneously with, or substantially simultaneously with, the lockout system 30 switching from the locked state to the unlocked state after the preselected time period has elapsed. Accordingly, the detectable output generated by the output element 32 may indicate to the patient or user of the injector 10 that the preselected time period has elapsed, that the injector 10 has been unlocked, and/or that the injector 10 is now operable by the patient or user to administer the drug 22. In embodiments where the lockout system 30 is omitted and/or the injector 10 is a manually-operated syringe, the detectable output generated by the output element 32 may only indicate to the patient or user of the injector 10 that the preselected time period has elapsed.

The output element 32 may be a mechanical device, a combination of mechanical devices, an electrical device, a combination of electrical devices, a chemical device, a combination of chemical devices, or any combination thereof (e.g., an electromechanical device, an electrochemical device, etc.). In some embodiments, the detectable output generated by the output element 32 may be a signal(s) capable of being sensed by the patient or other user of the injector 10 including, but not limited to, any one of, or any combination of: a sound, artificial light, a vibration, a change in color, or a change in the exterior shape or configuration of the injector 10. Additionally or alternatively, the detectable output generated by the output element 32 may be an electric or electromagnetic signal such as a wireless signal that is communicated over a network to an external or mobile computing device such as a smartphone or a server. In some embodiments, the detectable output generated by the output element 32 may be a digital signal.

In some embodiments, the output element 32 may include a flag member marked with a certain color(s), symbol(s), and/or text. The flag member and the housing 12 may be moveable (e.g., rotatable or translatable) relative to each other. Furthermore, the flag member may have a first position relative to the housing 12 prior to the elapse of the preselected time period, and a second position relative to the housing 12 after the elapse of the preselected time period. Furthermore, in embodiments where the timer 84 includes a spring or other mechanism that de-energizes over the duration of the preselected time period, the timer 84 may provide the motive force necessary for moving the flag member from the first position to the second position. In some embodiments, movement of the flag member between the first and second positions may occur continuously over the duration of the preselected time period. In other embodiments, the transition may occur relatively quickly or instantaneously near the end of the preselected time period.

In some embodiments, the flag member may be positioned inwardly of the exterior surface 54 of the housing 12 and hidden from view by the housing 12 in the first position. By contrast, in the second position, flag member may extend beyond the exterior surface 54 of the housing 12 or otherwise not be concealed by the housing 12. In some such embodiments, the flag member may be covered by a portion of the housing 12 in the first position, and aligned with an opening formed in the exterior surface 54 of the housing 12 in the second position so as to be visible to the patient or user of the injector 10. The flag member may have a different color than the exterior surface 54 of the housing 12, such that the resulting contrast provides meaning to the patient or user of the injector 10.

In some embodiments, the output element 32 may include a mechanical or electromechanical vibration unit that is activated to generate vibrations as the detectable output. In embodiments where sound is intended as the detectable output, the output element 32 may include a ratchet that creates an audible clicking sound as a toothed wheel or paddle wheel moves past a fixed pawl. In other variants, a speaker or alarm may be used to generate the sound.

In some embodiments, the output element 32 may include an emitter of artificial light such as a light emitting diode (LED) and/or an electronic display screen (e.g., a touchscreen). In some embodiments, the output element 32 may be configured to emit artificial light such that the output element 32 appears to glow; whereas, in other embodiments the output element 32 may be configured to emit artificial light such that it appears as a distinct and/or relatively small source of light.

While the foregoing embodiments have primarily been described in the context of the output element 32 being part of the injector 10, any of the foregoing embodiments of the output element 32 may be configured as part of a device that is separate from the injector 10. For example, the output element 32 may be part of an external or mobile computing device such as a smartphone, smartwatch, or personal computer. Such an external or mobile computing device may be free to move independently of the injector 10. In certain such embodiments, the detectable output may take the form of an email, push notification, SMS message, and/or phone call. In another embodiment, the output element 32 may be incorporated into the protective disposable packaging in which the injector 10 is shipped or stored by a manufacturer or supplier and which is removed by the patient or user prior to use of the injector 10.

Also, in some embodiments, the output element 32 and the timer 84 may be integrally formed with each other such that they form a single, unitary structure or substance. For example, the output element 32 and the timer 84 may be defined by a single chemical substance which, upon being initiated, begins to undergo a chemical reaction at a predicted or expected rate, with the chemical reaction finishing upon the expiration of the preselected time period. As a result of the chemical reaction, the visual appearance of the substance may change, thereby indicating to the patient or user of the injector 10 that the preselected time period has elapsed. The change in the visual appearance of the substance can be any one or combination of: a change in color, a change from being colorless to being colored or vice versa, a change in transparency (e.g., a change from being clear to being opaque), a change in text, and a change in symbols. In some embodiments, text and/or a symbol such a company logo may appear only after the preselected time period has elapsed. The change in visual appearance may occur gradually over the duration of the preselected time period or suddenly at the completion of the preselected time period. In some embodiments, the chemical substance may be included on a label adhered to the exterior surface 54 of the housing 12, or may be part of the protective disposable packaging in which the injector 10 is shipped or stored by a manufacturer or supplier and which is removed by the patient or user prior to use of the injector 10. In some embodiments, the chemical substance may be a light-activated substance that is initially covered by a removable element such that the chemical substance is not exposed to ambient light. Upon removal of the removable element, the chemical substance may be exposed to ambient light. This, in turn, may cause the chemical substance to undergo a color-changing chemical reaction, upon the completion of which corresponds to the end of the preselected time period.

Figure 6:
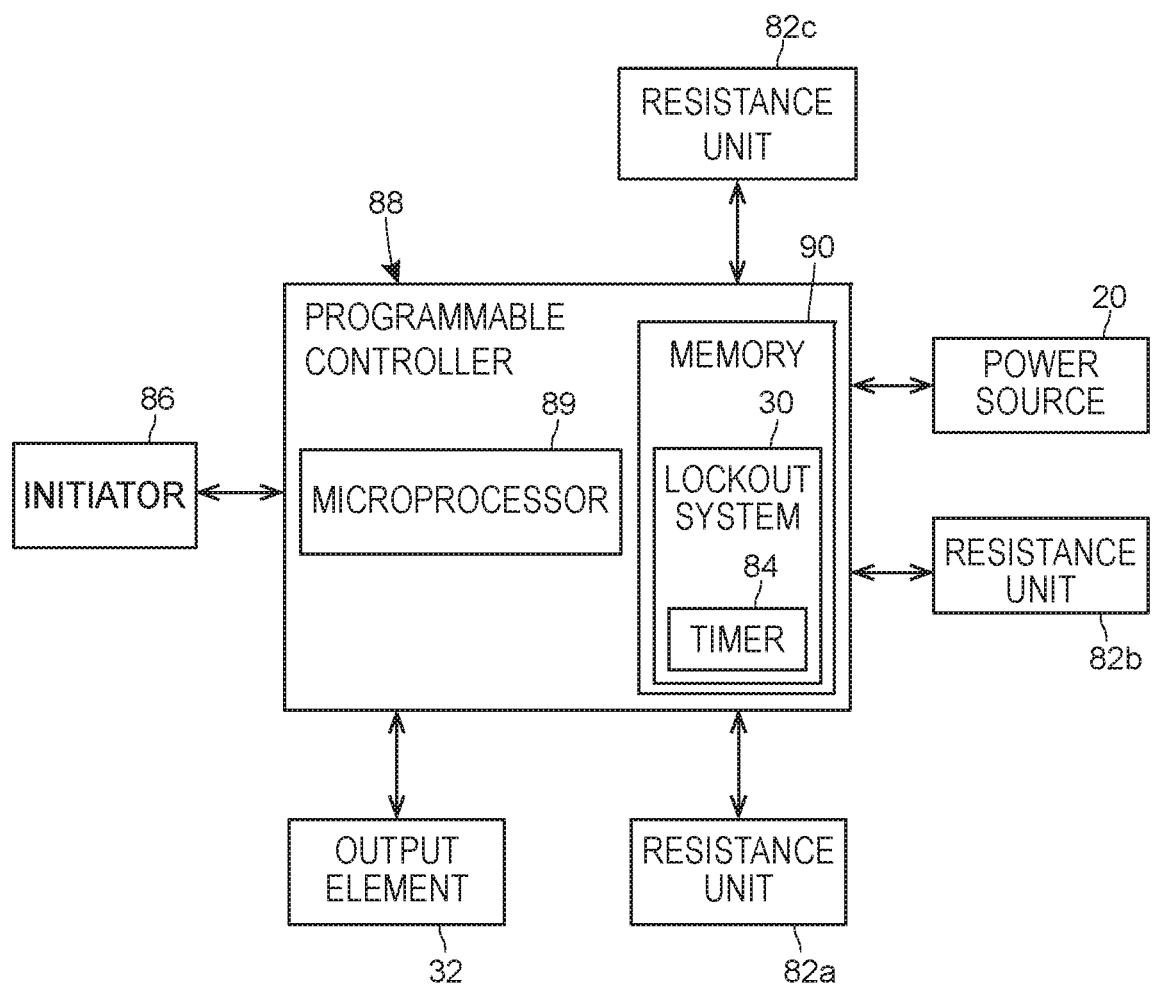
FIG. 6 is a schematic representation of an embodiment of a programmable controller for use with an injector in accordance with principles of the present disclosure.

Turning to FIG. 6, illustrated is a programmable controller 88 that may be used for controlling or implementing various automated features of the injector 10 including any one of, or any combination of, the energy source 20, lockout system 30, output element 32, resistance units 82a-c, timer 84, or other features of the injector 10. The programmable controller 88 may be disposed entirely within the interior space 52 of the housing 12, or it may be distributed across multiple devices including the injector 10. The programmable controller 88 may be in electric communication with, via a wired or wireless connection, one or more of the energy source 20, the output element 32, resistance units 82a-c, or other features of the injector. The programmable controller 88 may include at least a processor 89 (e.g., a microprocessor) and a memory 90 which are in communication with or integrated with each other. The programmable controller 88 may be powered by an electrical power supply incorporated into the injector 10 such as a battery. The memory 90 may include a non-transitory computer-readable storage medium configured to store data, including, for example, non-transitory computer-readable instructions constituting one or more services or programs and any data operated on or produced by such services or programs. The memory 90 may store the data on a volatile (e.g., RAM) and/or non-volatile memory (e.g., a hard disk), and may be a removable or non-removable memory. The processor 89 may be configured to fetch and execute the instructions stored in the memory 90 in order to perform various functions of, for example, the lockout system 30 and/or the output element 32.

In some embodiments, the lockout system 30 may be a set of non-transitory computer-executable instructions programmed into the memory 90 and which are executed by the processor 89 in response to actuation of the initiator 86 by the patient or user of the injector 10. Execution of these instructions may cause the programmable controller 88 to determine whether a preselected time period has elapsed, and if so, transmit an electrical control signal to one or more of the resistance units 82a-c causing them to switch to a disengaged state where they permit movement of one or more of the removable cap 58, inner sleeve 48, or trigger member 78. Simultaneously or immediately thereafter, the programmable controller 88 may transmit an electrical control signal to the output element 32 to cause the output element 32 to produce the detectable output. In such an embodiment, the programmable controller 88 would perform the function of the timer 84.

According to those embodiments wherein the lockout system 30 and/or the timer 84 is defined by the programmable controller 88, the configuration of the lockout system 30 and/or timer 84 may correspond to the programming of the programmable controller 88.

In some embodiments, the patient or user may initiate operation of the programmable controller 88 so that it executes the programming stored in the memory 90 by actuating or otherwise interacting with the initiator 86. Furthermore, in some embodiments, the initiator 86 may be the sole means by which the patient can interact with the programmable controller 88. In embodiments where the injector 10 is configured for single-use and disposal immediately thereafter, the programmable controller 88 may be programmed to be initiated only once.

In some embodiments, the memory 90 of the programmable controller 88 may be programmed prior to disposing, and optionally sealing, the programmable controller 88 within the housing 12 of the injector 10. Thus, once the programmable controller 88 is disposed and optionally sealed within the housing 12, the programmable controller 88 may not be re-programmed.

In embodiments where the actuator 76 is an electric motor, the programmable controller 88 may transmit electrical signals to the electric motor and/or the energy source 20 for controlling the start, stop, speed, and/or other operational characteristics of the electric motor.

Although the controller 88 described above is a programmable one, alternative embodiments may include a controller that is a mechanical device, a combination of mechanical devices, a hardwired circuit device, a combination of hardwired circuit devices, or any combination thereof.

A method of operation of the injector 10 will now be described with reference to FIGS. 2-5. Initially, the patient or user may obtain the injector 10 from his or her healthcare provider, such as a doctor or pharmacist. The injector 10 may be a pre-loaded and pre-filled device such that the reservoir 16 is filled and loaded into the injector 10 prior to the patient or user obtaining the injector 10 from the healthcare provider. Upon receipt by the patient or user, the lockout system 30 may already be configured in the locked state and/or the timer 84 may already be configured with the preselected time period. By virtue of being configured in the locked state, the lockout system 30 may be configured to prevent movement of the delivery member 14 relative to the housing 12 and/or activation of the energy source 20 via, for example, one or more of the resistance units 82*a-c*.

Next, the patient or user may initiate the timer 84 by actuating or otherwise interacting with the initiator 86. According to those embodiments wherein the initiator 86 is a depressible button, initiating the timer 84 may involve the patient or user depressing the button into the housing 12. Upon initiation, the timer 84 may start the preselected time period and automatically determine when the preselected time period has elapsed. The timer 84 may do this only once according to its configuration in embodiments where the injector 10 is for single-use. As mentioned above, according to at least one embodiment, the length of the preselected time period may not be less than 24 hours. The length of the preselected time period may vary according to the circumstances of the particular application, although the configuration of the timer 84 in this regard may not be adjusted by the patient or user, or even the healthcare provider in certain embodiments. Also, in certain alternative embodiments, the healthcare provider, in lieu of the patient or user, may be relied upon for initiating the timer 84 via the initiator 86.

In still further alternative embodiments, the injector 10 may be obtained by the patient or user with the lockout system 30 configured in the unlocked state. In such alternative embodiments, the patient or user may place the lockout system 30 in the locked state by actuating or otherwise interacting with the initiator 86. Thus, the initiator 86 may simultaneously configure the lockout system 30 in the locked state and initiate the countdown by the timer 84.

Immediately or shortly after the preselected time period has elapsed, the lockout system 30 may automatically change from the locked state to the unlocked state, thereby permitting movement of the delivery member 14 relative to the housing 12 and/or activation of the energy source 20. The lockout system 30 may change from the locked state to the unlocked state only once according to its configuration in embodiments where the injector 10 is for single-use. In some embodiments, the lockout system 30 may implement this change by automatically controlling one or more of the resistance units 82*a-c* to switch from an engaging state to a disengaging state. For example, the lockout system 30 may control the resistance unit 82*c* to disengage from the trigger member 78, thereby permitting movement of the trigger member 78 to activate the energy source 20.

Also upon the expiration of the preselected time period, the output element 32 may output the detectable output to notify the patient or user that the preselected time period has elapsed and/or that the injector is now unlocked. In embodiments where the lockout system 30 is omitted, the output element 32 may notify the patient or user that the preselected time period has elapsed without an indication about the unlocked state.

Next, if it has not already been done, the patient or user may remove the removable cap 58 from the housing 12. The shield 51, which may be gripped by the interior of the removable cap 58, may be removed together with the removable cap 58, thereby exposing the pointed end 18 of the delivery member 14. Then, as shown in FIG. 3, the patient or user may position the injector 10 with the distal end of the inner sleeve 48 in contact with the patient's skin 92 at an injection site 93. Subsequently, while grasping the proximal end 40 of the housing 12 in a single hand, the patient or user may push the injector 10 in the distal direction toward the patient's skin 92 at an injection site 93. This motion may cause the inner sleeve 48 to retract into the outer sleeve 46, which, in turn, may allow for the pointed end 18 of the delivery member 14, whose position may remain stationary relative to the outer sleeve 46, to pierce the patient's skin 92 at the injection site 93 until the pointed end 18 of the delivery member 14 is disposed in, for example, the patient's subcutaneous tissue (see FIG. 4). The delivery member 14 may transition from the initial state to the delivery state as a result of retraction of the inner sleeve 48.

Figure 5:
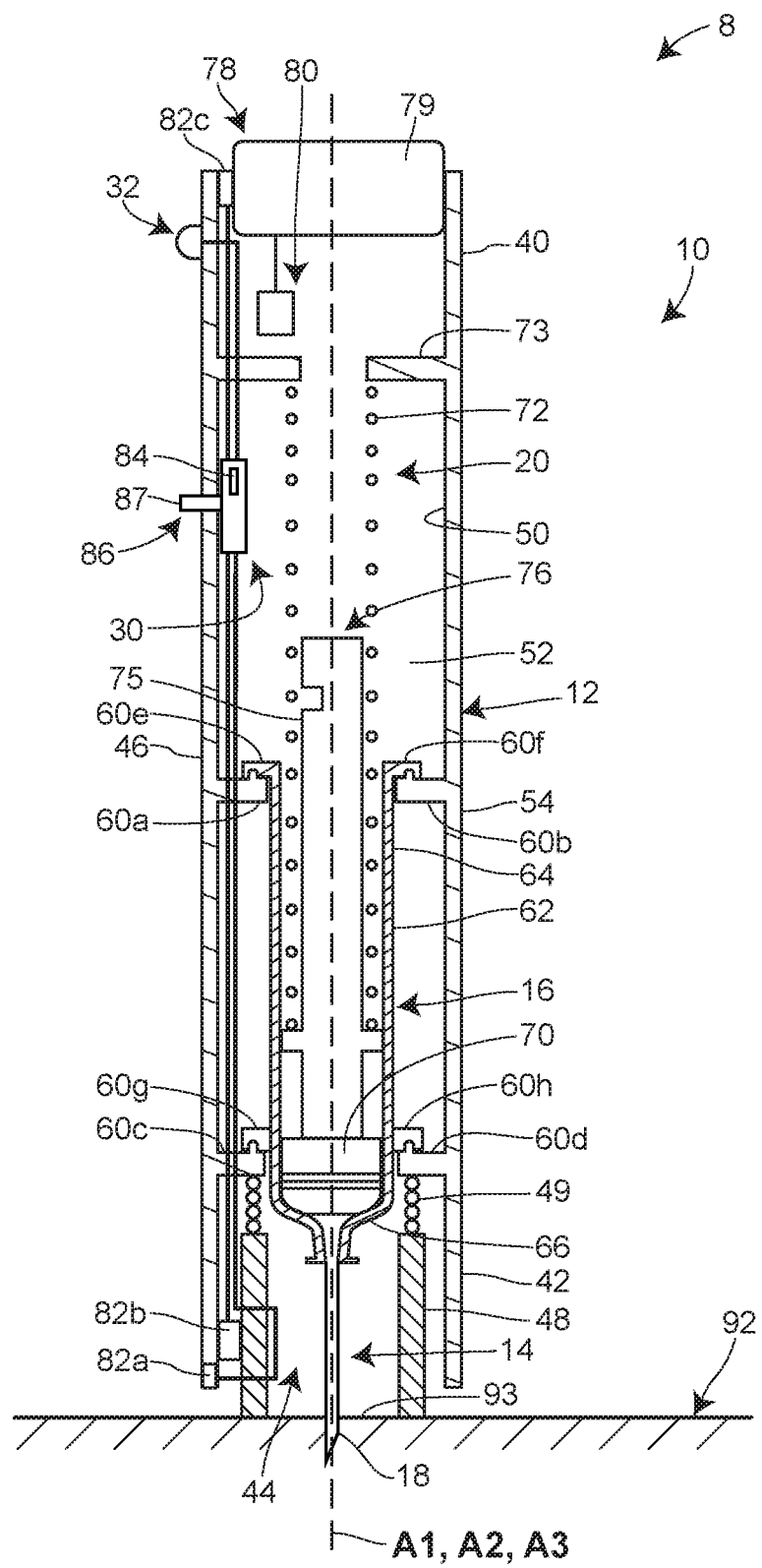

Next, as illustrated in FIG. 5, the patient or user may activate the energy source 20 by actuating or otherwise interacting with the trigger member 78. Upon activation, the energy source 20 may output its stored energy to automatically actuate the reservoir 16 to deliver the volume of the drug 22 to the patient as a single bolus. This may involve the energy source 20 causing the stopper 70 to move in a single continuous (i.e., uninterrupted) motion or stroke from an initial position near the proximal end 64 of the reservoir 16 (see FIG. 4) to a final position near the distal end 66 of the reservoir 16 where the stopper 70 contacts a proximally-facing interior surface of the reservoir 16 (see FIG. 5). As a consequence, the entire volume, or substantially all of the volume, of the drug 22 contained in the reservoir 16 may be expelled through the delivery member 14 and into the patient all at once. After drug delivery is complete, the patient or user may remove the delivery member 14 from the patient's tissue and, if the injector 10 is intended for single-use, dispose or throw away the entire injector 10. In embodiments where the inner sleeve 48 is biased towards a deployed position, removal of the injector 10 from the patient's skin may result in the inner sleeve 48 moving back to the deployed position, thereby covering and preventing accidental sticks with the pointed end 18 of the delivery member 14.

In addition to this general process, the injector 10 may include other suboperations. For example, according to certain embodiments, the injector 10 may automatically provide an end-of-dose indicator.

In alternative embodiments, the delivery member 14 may not be inserted into the patient until after the energy source 20 is activated by the patient or user. Additionally, according to certain embodiments, the energy source 20 may automatically retract the delivery member 14 so that the pointed end 18 is disposed within the interior space 52 of the housing 12 after drug delivery is complete. In still further alternative embodiments, retraction of the inner sleeve 48 into the outer sleeve 46 may activate the energy source 20 to automatically insert the delivery member 14 into the patient and/or actuate the reservoir 16 to expel the volume of the drug 22.

In alternative embodiments, the injector 10 or a portion thereof may be reusable. In such embodiments, the reservoir 16 and the delivery member 14 (which may be integrated in the form of a syringe) may be removed from the housing 12 after the completion of drug delivery and replaced by the patient or user with another reservoir and/or delivery member.

FIGS. 7-16 illustrate variations of the embodiments of the system described in connection with FIGS. 1-6. The embodiments in FIGS. 7-16 are similar in certain respects to the embodiments described in connection with FIGS. 1-6. Instead of repeating the details of the structure and/or function which are common between the embodiments of FIGS. 1-6 and the embodiments of FIGS. 7-16, only the details of the structure and/or function that differentiate the embodiments of FIGS. 7-16 from the embodiments of FIGS. 1-6 will be discussed in connection with FIGS. 7-16.

FIGS. 7 and 8 depict an embodiment of an injector 110 wherein the initiator is defined at least in part by a frangible peel tab 186, the timer is defined at least in part by a rotationally-biased carrier sleeve 184, and the lockout system is defined at least part by a spring-loaded pin 130. Referring to FIG. 7, the spring-loaded pin 130 rotationally and axially locks the carrier sleeve 184 relative to an inner sleeve portion 158a of the removable cap 158 to define the locked state of the lockout system. This is accomplished by receiving a radially inward end of the spring-loaded pin 130 in an opening formed in the inner sleeve portion 158a of the removable cap 158. The spring-loaded pin 130 is biased to retract from this opening, but is initially prevented from doing so by an inner wall of the housing 112. In addition, an interlock member 186a defined by an end of the frangible peel tab 186 initially rotationally locks the carrier sleeve 184 relative to the housing 112, which retains a torsion spring or other rotational biasing member bearing upon the carrier sleeve 184 in an energized state.

Upon removal of the frangible peel tab 186 from the housing 112 by a patient or other user of the injector 110, the interlock member 186a no longer prevents rotational movement of the carrier sleeve 184 relative to the housing 112. Accordingly, the torsion spring or other rotational biasing member bearing upon the carrier sleeve 184 is released and begins to rotate the carrier sleeve 184 relative to the housing 112 around a longitudinal axis A1 of the housing 112 in the counter-clockwise direction in FIG. 7. Because the spring-loaded pin 130 is received in the opening formed in the inner sleeve portion 158a of the removable cap 158, the removable cap 158 will rotate jointly together with the carrier sleeve 184. This joint rotation continues until the spring-loaded pin 130 reaches a rotational position where it is aligned with a recess 112a formed in the inner surface of the housing 112. This recess 112a provides clearance for the spring-loaded pin 130 to retract from the opening formed in the inner sleeve portion 158a of the removable cap 158. As a result of this retraction, the removable cap 158 is unlocked from the carrier sleeve 184 and can be removed from the housing 112. In this embodiment, the amount of time required for the carrier sleeve 184 to rotate from the initial position shown in FIG. 7 to the position where the spring-loaded pin 130 is aligned with the recess 112a corresponds to the preselected time period.

Figure 9C:
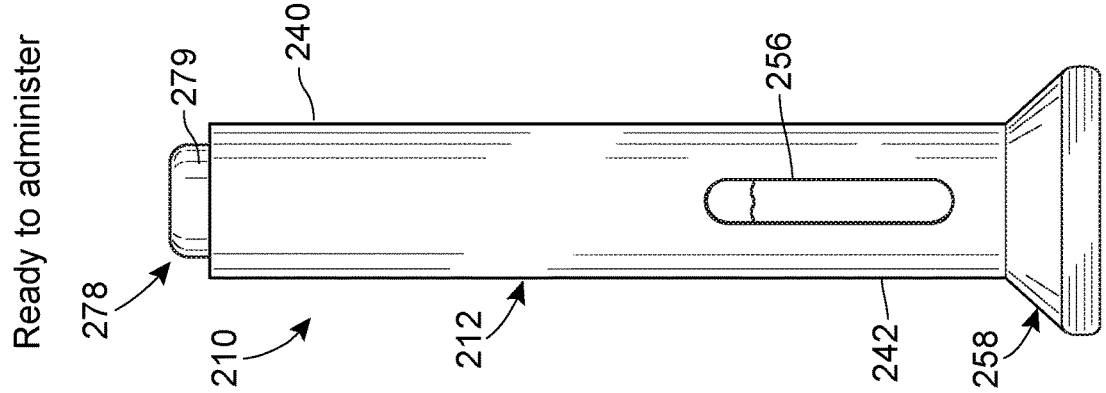
FIG. 9C is a perspective view of the injector of FIG. 9A after the preselected time period has elapsed.
Figure 9B:
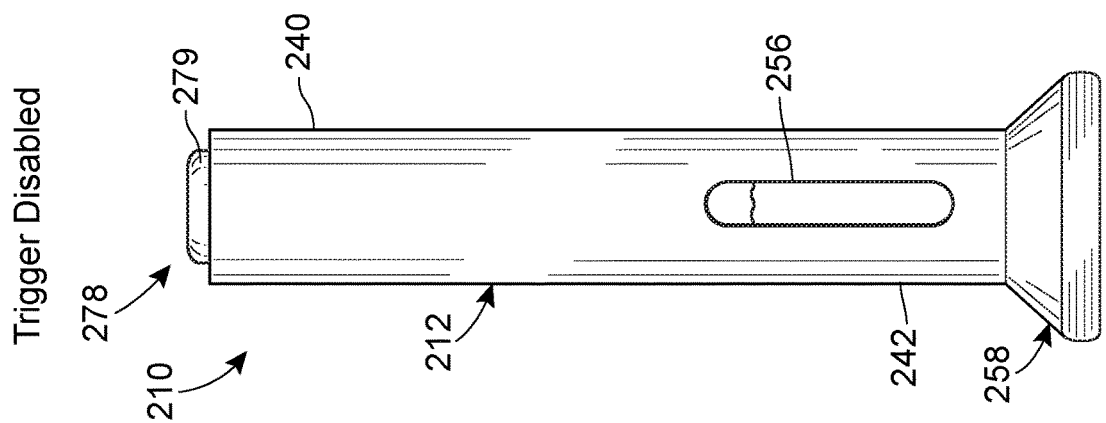
FIG. 9B is a perspective view of the injector of FIG. 9A during the preselected time period.
Figure 9A:
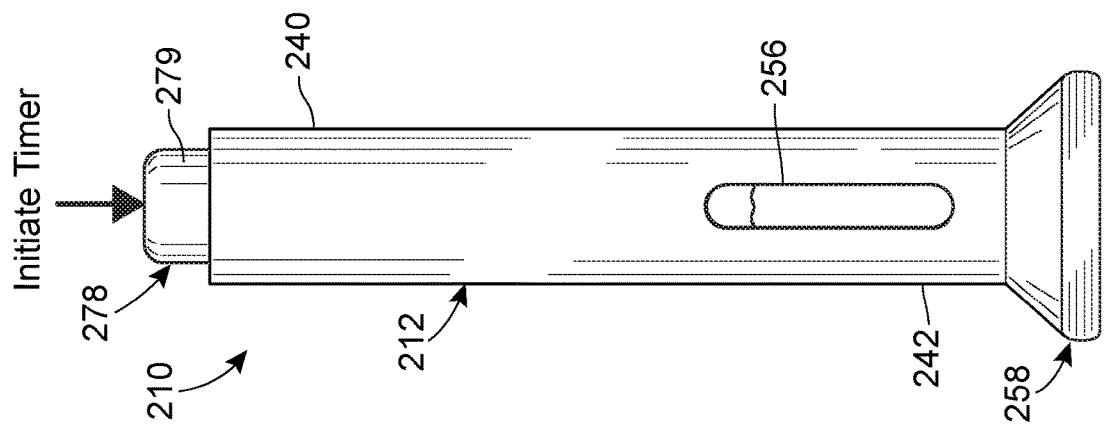
FIG. 9A is a perspective view of another embodiment of a system including an injector in accordance with principles of the present disclosure, prior to the start of a preselected time period.

FIGS. 9A-9C illustrate an embodiment of an injector 210 wherein a trigger member 278, which is configured to activate the energy source of the injector 210 upon application of a force by the patient or user, is additionally configured as the initiator for the timer. In addition, the trigger member 278 may be configured to permit the patient or user to place the lockout system in the locked state simultaneously with initiation of the timer. More particularly, the trigger member 278 includes a button 279 having a first position wherein the trigger member 278 extends through an opening formed in the proximal end 240 of the housing 212, and a second position wherein the button 279 is retracted into the housing 212 away from the first position. A biasing member such as a spring may be configured to urge the button 279 toward the first position. Initially, upon un-packaging the injector 210 for example, the button 279 may be arranged in the first position, as shown in FIG. 9A. The patient or user manually presses the button 279 into the housing 212 in the distal direction, moving the button 279 from the first position to the second position, and causing the button 279 or another portion of the trigger member 278 to initiate operation of the timer. As a consequence, the timer may begin to monitor whether the preselected time period has elapsed. The initial movement of the button 279 may also simultaneously configure the lockout system in the locked state. In the present embodiment, the locked state corresponds to preventing proximal movement of the button 279 relative to the housing 212. A resistance unit such as the above-described resistance unit 82c can be configured for this purpose. In the locked state, the button 279 is retained in the second position, as illustrated in FIG. 9B. Accordingly, the patient or user may be prevented from pressing the button 279 a second time, which would cause the button 279 to activate the energy source. Upon the elapse of the preselected time period, the lockout system may automatically change from the locked state to the unlocked state, thereby permitting the button 279 to return to its first position, as shown in FIG. 9C. Subsequently, the patient or user may press the button 279 in the distal direction a second time, moving the button 279 from the first position to the second position, and causing the button 279 or another portion of the trigger member 278 to activate the energy source. Activation of the energy source, as discussed above, may cause the energy source to output energy for moving the delivery member of the injector 210 from an initial state to a delivery state and/or cause the energy source to output energy for actuating a reservoir to deliver a volume of a drug to the patient as a single bolus.

Figure 10:
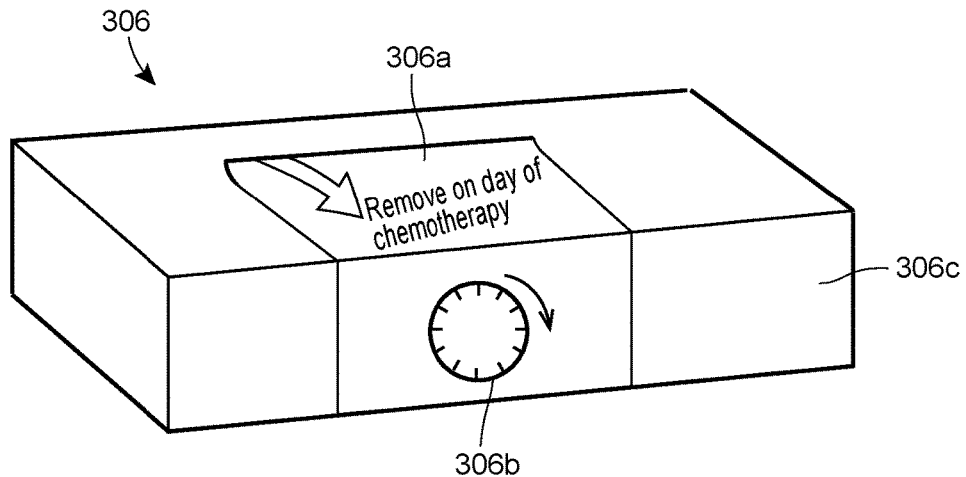
FIG. 10 is a perspective view of another embodiment of a system including an injector in accordance with principles of the present disclosure.

FIG. 10 illustrates an embodiment of disposable packaging 306 in which an injector is shipped or stored by a manufacturer or supplier and which is removed by the patient or user prior to use of the injector. In the present embodiment, the initiator, timer, and/or output element may be defined by or otherwise incorporated into the disposable packaging 306. More particularly with respect to FIG. 10, the packaging 306 may include a removable outer label 306a which defines the initiator. The patient or user may pull off or otherwise detach the removable outer label 306a from a remainder of the disposable packaging 306 in order to initiate the timer. As a consequence, the timer may begin to monitor whether the preselected time period has elapsed. The output element may be defined by a rotatable dial 306b disposed at an exterior surface 306c of the disposable packaging 306. Upon the expiration of the preselected time, the rotatable dial 306b may have a rotational position indicating to the patient or user that use of the injector, which may still be disposed within the interior space of the disposable packaging 306, is appropriate. A benefit of incorporating the initiator, timer, and/or output element into the disposable packaging 306 is that the timer and notification functionalities may be implemented without having to modify the design of an existing injector.

Figures 11A, 11B, 12:
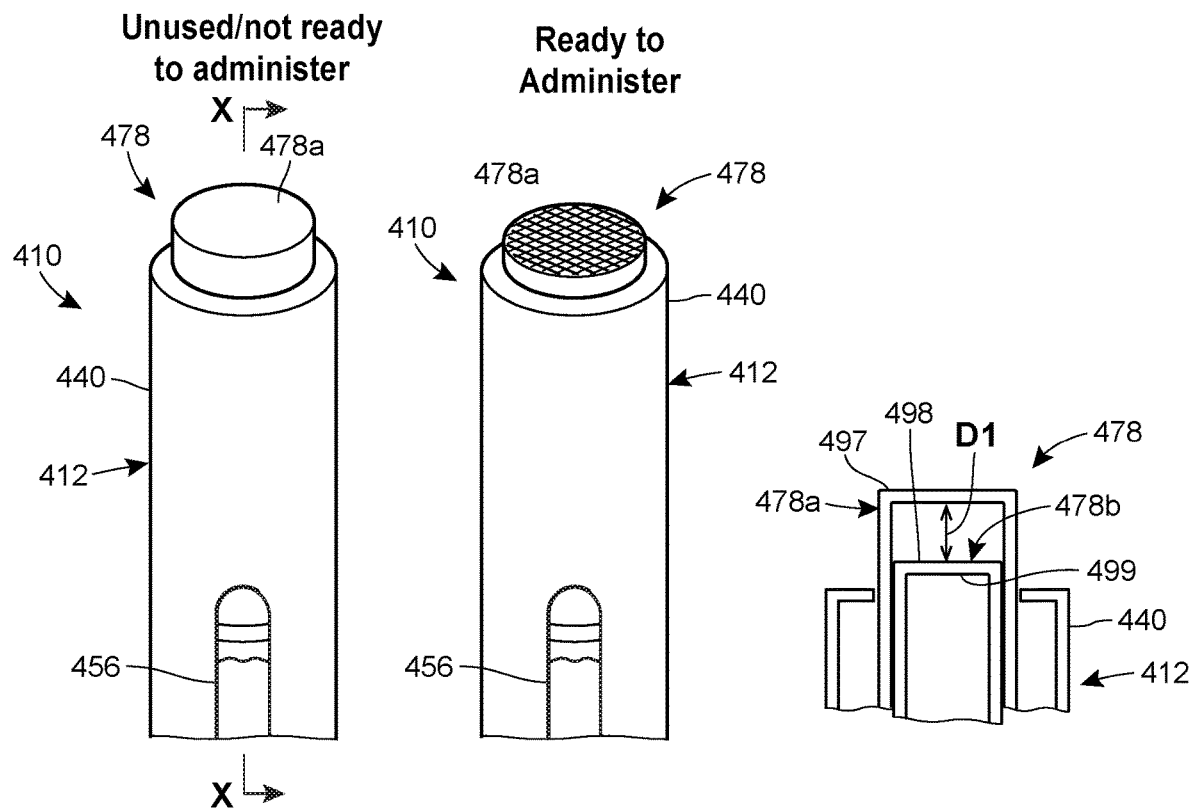
FIG. 11A is a perspective view of another embodiment of a system including an injector in accordance with principles of the present disclosure, prior to the start of a preselected time period.
FIG. 11B is a perspective view of the injector of FIG. 11B after the preselected time period has elapsed.
FIG. 12 is a cross-sectional view taken along line X-X of FIG. 11A.

FIGS. 11A-12 illustrate an embodiment of an injector 410 wherein a trigger member 478, which is configured to activate the energy source of the injector 410 upon application of a force by the patient or user, is additionally configured as the output element for notifying the patient or user of the expiration of the preselect time period. More particularly, the trigger member 478 may include an exterior button or sleeve 478a and an interior button or sleeve 478b, as seen in the cross-sectional view of FIG. 12. The inner sleeve 478b may be slidably disposed within an interior space defined by the outer sleeve 478a. A proximal end 497 of the outer sleeve 478a may be constructed of a translucent (e.g., frosted or semi-opaque) material, and a proximally-facing exterior surface 498 of a proximal end 499 of the inner sleeve 478b may be marked with a bright color, pattern, or other visual marking.

The outer sleeve 478a and the inner sleeve 478b each may be configured to move relative to the housing 412. The outer sleeve 478a may have a first position wherein the outer sleeve 478a extends through an opening formed in the proximal end 440 of the housing 412 (see FIGS. 11A and 12), a second position wherein the outer sleeve 478a is retracted into the opening away from the first position (see FIG. 11B), and a third position wherein the outer sleeve 478a is further retracted into the opening away from the second position. The inner sleeve 478b may have a first position wherein the inner sleeve 478b extends through the opening formed in the proximal end 440 of the housing 412 (see FIG. 12), and a second position wherein the inner sleeve 478b is retracted into the opening away from the first position.

Prior to use, the outer sleeve 478a and the inner sleeve 478b may be arranged in their respective first positions, with the proximally-facing exterior surface 498 of the proximal end 499 of the inner sleeve 478b being spaced apart from an interior surface of the proximal end 497 of the outer sleeve 478a by a distance D1, as seen in FIG. 12. As a consequence, the translucent material of the outer sleeve 478a may obscure or otherwise make it very difficult for the patient or user to see the marking on the proximally-facing exterior surface 498 of a proximal end 499 of the inner sleeve 478b.

Initiating the timer of the injector 410 may activate a mechanism for automatically moving the outer sleeve 478a in the distal direction from its first position to its second position. The amount of time it takes for the outer sleeve 478a to move from the first position to the second position may correspond to the preselected time period. During this movement of the outer sleeve 478a, the inner sleeve 478b may remain stationary. As a result, when the outer sleeve 478a reaches its second position, the distance D1 may be reduced or non-existent. With little or no gap between the outer sleeve 478a and the inner sleeve 478b, the obscuring effect of the outer sleeve 478a is diminished, thereby revealing the marking on the proximally-facing exterior surface 498 of the inner sleeve 478b. The marking may indicate to the patient or user that the preselected time period has elapsed, such that patient or user is made aware that the time has arrived for using the injector 410 to inject the drug. Subsequently, the patient or user may activate the energy source by manually depressing the outer sleeve 478a in the distal direction into the housing 412, thereby moving the outer sleeve 478a from its second position to its third position. Because the outer sleeve 478a may contact the proximally-facing exterior surface 498 of the inner sleeve 478b in the second position, further distal movement of the outer sleeve 478a may push the inner sleeve 478b from its first position to its second position. Such movement of the inner sleeve 478b may activate the energy source of the injector 410, thereby releasing energy for moving the delivery member of the injector 410 from an initial state to a delivery state and/or actuating a reservoir to deliver a volume of a drug to the patient as a single bolus.

Figure 13:
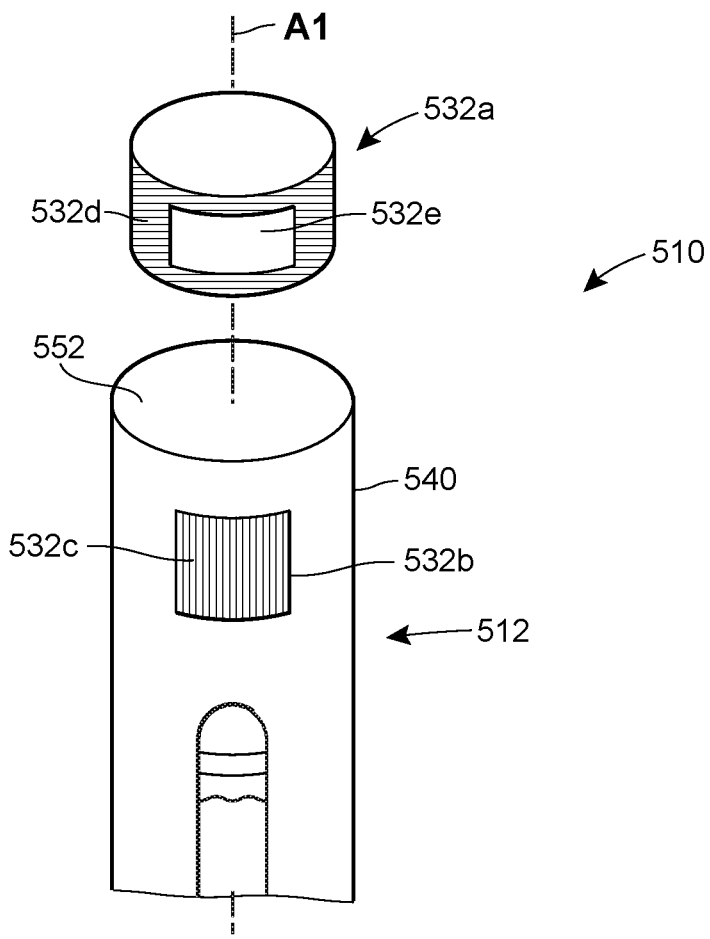
FIG. 13 is an assembly view of another embodiment of a system including an injector in accordance with principles of the present disclosure.

FIG. 13 illustrates an embodiment of an injector 510 wherein the output element is defined at least in part by a rotatable sleeve 532a disposed in the interior space 552 of the housing 512 and which is rotatable around the longitudinal axis A1 of the housing 512. An opening 532b may be formed in a circumferential wall of the housing 512 and covered with a transparent film 532c having a colored tint (e.g., a red tint). The rotatable sleeve 532a may be positioned behind the transparent film 532c, such that the rotatable sleeve 532a is aligned along the longitudinal axis A1 of the housing 512 with the transparent film 532. Furthermore, the rotatable sleeve 532a may have an outer circumferential surface 532d possessing a different color than the color of the tint of the transparent film 532c. Moreover, an opening 532e may formed in the outer circumferential surface 532d of the rotatable sleeve 532a.

The rotatable sleeve 532a may be configured to rotate relative to the housing 512 between a first rotational position and a second rotational position gradually over the duration of the preselected time period, or at all at once at the end of the preselected time period. In some embodiments, the rotational motion of the rotatable sleeve 532a may be accomplished via a spring-based mechanism, such as, for example, a mechanism driven by a torsion spring. In the first rotational position, the opening 532e may be rotationally aligned with the transparent film 532c, such that the opening 532e is positioned directly behind the transparent film 532c. Accordingly, when looking through the transparent film 532c, the patient or user may see an image tinted by the color of the transparent film 532c. In a preferred embodiment, the color of the tint of the transparent film 532c is red, to indicate to the patient or user that the time for use of the injector 510 has yet to arrive. In the second rotational position, corresponding to the end of the preselected time period, the colored outer circumferential surface 532d of the rotatable sleeve 532a (instead of the opening 532e) may be rotationally aligned with the transparent film 532c. As a consequence, when looking through the transparent film 532c, the patient or user may see an image of the colored outer circumferential surface 532d, but tinted by the color of the transparent film 532c. In a preferred embodiment, the outer circumferential surface 532d of the rotatable sleeve 532a is blue. As a consequence, the outer circumferential surface 532d may appear to have a green color when seen through the red-tinted transparent film 532c. This green color may indicate to the patient or user that the preselected time period has elapsed, such that patient or user knows that the time has arrived for using the injector 510 to inject the drug. In some embodiments, an emitter of artificial light may be positioned within the interior space 552 of the housing 512 for backlighting purposes.

Figure 14A:
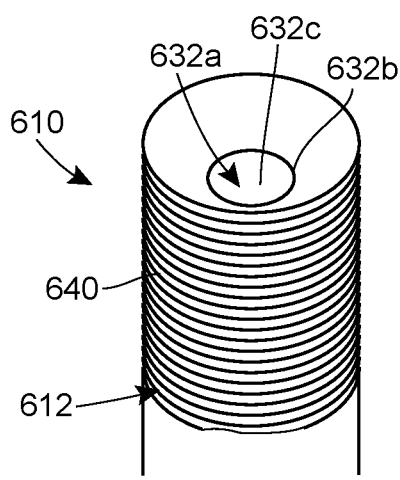
FIG. 14A is a perspective view of another embodiment of a system including an injector in accordance with principles of the present disclosure, prior to the elapse of a preselected time period.
Figure 14B:
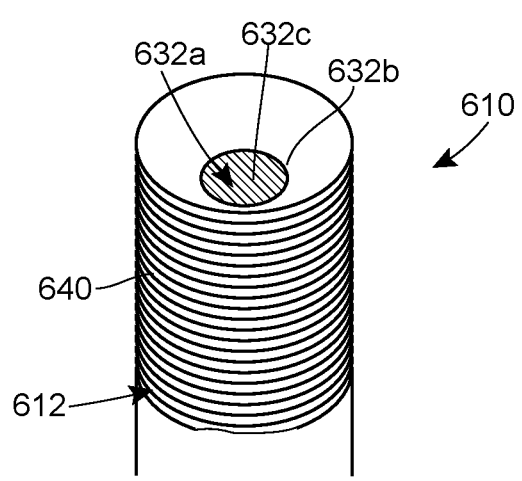
FIG. 14B is a perspective view of the injector of FIG. 14A after the preselected time period has elapsed.

FIGS. 14A and 14B illustrate another embodiment of an injector 610 wherein the output element is defined at least in part by a rotatable disk 632a disposed in the interior space 652 of the housing 612 and which is rotatable around the longitudinal axis A1 of the housing 612. An opening 632b may be formed in a proximally-facing end surface of the proximal end 640 of the housing 612. The rotatable disk 632a may be positioned behind the opening 632b. A first portion 632c of a proximally-facing end surface of the disk 632a may have a first color, and a second portion 632d of the proximally-facing end surface of the disk 632a may have a second color. The first color may differ from the second color. In some embodiments, the first color may be white and/or the same as a color of an exterior surface of the proximal end 640 of the housing 612; and the second color may be green and/or differ from the color of the exterior surface of the proximal end 640 of the housing 612.

The rotatable disk 632a may be configured to rotate relative to the housing 612 between a first rotational position and a second rotational position gradually over the duration of the preselected time period, or all at once at the end of the preselected time period. In some embodiments, the rotational motion of the rotatable sleeve 632a may be accomplished via a spring-based mechanism, such as, for example, a mechanism driven by a torsion spring. In the first rotational position, the first portion 632c of the rotatable disk 632a may be rotationally aligned with the opening 632b in the proximal end 640 of the housing 612, as illustrated in FIG. 14A. Accordingly, when looking through the opening 632b, the patient or user may see the first color of the first portion 632c of the rotatable disk 632a. The first color may indicate to the patient or user that the time for use of the injector 610 has yet to arrive. In the second rotational position, corresponding to the end of the preselected time period, the second portion 632d of the rotatable disk 632a may be rotationally aligned with the opening 632b, as depicted in FIG. 14B. As a consequence, when looking through the opening 632b, the patient or user may only see the second color of the second portion 632d of the rotatable disk 632a. The second color may indicate to the patient or user that the preselected time period has elapsed, such that patient or user knows that the time has arrived for using the injector 610 to inject the drug.

In the embodiment depicted in FIGS. 14A and 14B, the opening 632b is offset from the longitudinal axis A1 of the housing 612. In alternative embodiments, the opening 632b may be centered about or otherwise aligned with the longitudinal axis A1. In such alternative embodiments, the rotational axis of the rotatable disk 632a may be offset from the longitudinal axis A1 of the housing 612, and the surface area of the rotatable disk 632a may be smaller than a cross-sectional area of the proximal end 640 of the housing 612. Furthermore, a first half of the rotatable disk 632a may have a first color or marking and may occupy the opening 632b when the rotatable disk 632a is arranged in a first rotational position prior to the elapse of the preselected time period. A second half of the rotatable disk 632a may have a second color or marking and may occupy the opening 632b when the rotatable disk 632a is arranged in a second rotational position after the elapse of the preselected time period.

As an alternative to the rotatable disk 632a, a flexible tape may be positioned inside the proximal end 640 of the housing 612 and may extend across the opening 632b between two rollers. A first end of the tape may have a first color or marking, and a second end of the tape may have a second color or marking. Rotating one of the rollers may cause the tape to be unwound from the other one of the rollers and conveyed across the opening 632b in a direction that is perpendicular to the longitudinal axis A1. Before the start of the preselected time period, the first end of the tape may be positioned beneath and thus visible through the opening 632b. After the preselected time period has elapsed and/or during the preselected time period, the rollers may be rotated to cause the second end of the tape to be visible through the opening 632b.

Figure 15C:
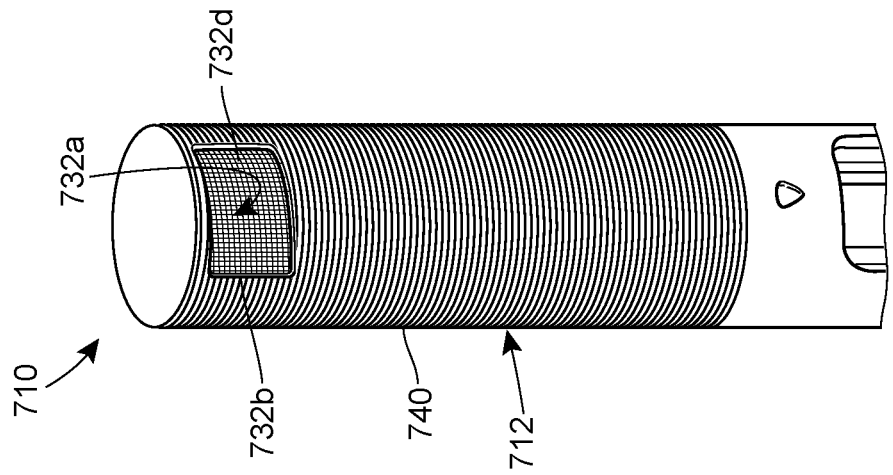
FIG. 15C is a perspective view of the injector of FIG. 15A after the preselected time period has elapsed.
Figure 15B:
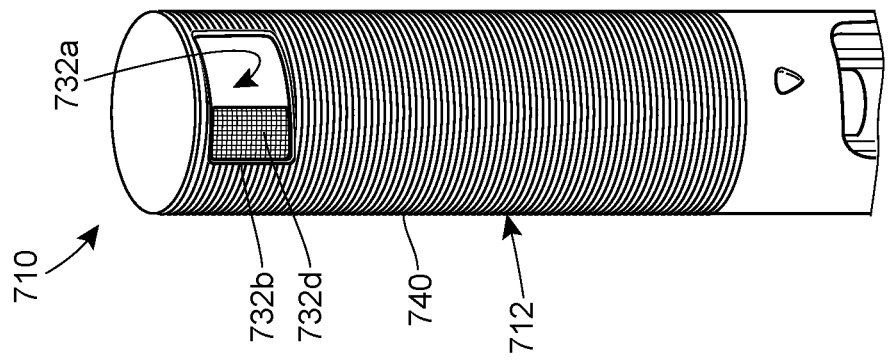
FIG. 15B is a perspective view of the injector of FIG. 15A during the preselected time period.
Figure 15A:
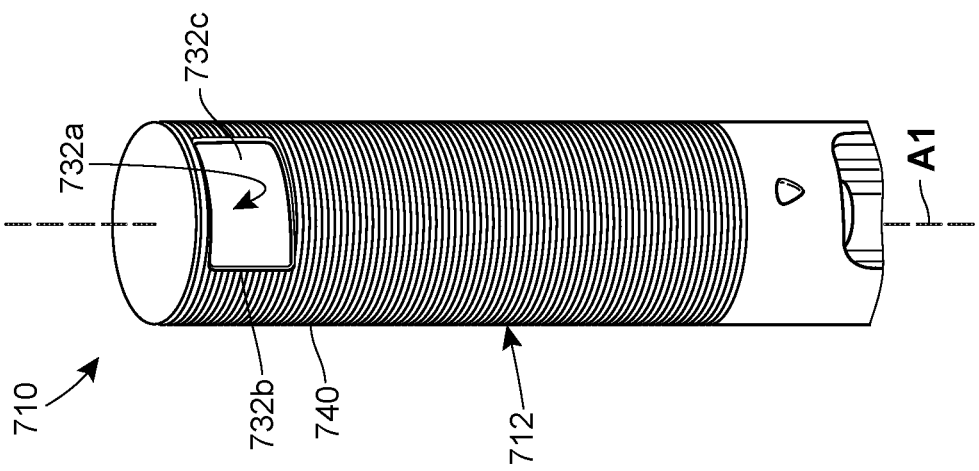
FIG. 15A is a perspective view of another embodiment of a system including an injector in accordance with principles of the present disclosure, prior to the start of a preselected time period.

FIGS. 15A-15C illustrate another embodiment of an injector 710 wherein the output element is defined at least in part by a rotatable sleeve 732a disposed in the interior space 752 of the housing 712 and which is rotatable around the longitudinal axis A1 of the housing 712. An opening 732b may be formed in a circumferential wall of the housing 712. The rotatable sleeve 732a may be positioned behind the opening 732b, such that the rotatable sleeve 732a is aligned along the longitudinal axis A1 of the housing 712 with the opening 732b. A first portion 732c of a circumferential outer surface of the rotatable sleeve 732a may have a first color, and a second portion 732d of the circumferential outer surface of the rotatable sleeve 732a may have a second color. The first color may be different from the second color. In some embodiments, the first color may be white and/or the same as a color of an exterior surface of the proximal end 740 of the housing 712; and the second color may be yellow and/or differ from the color of the exterior surface of the proximal end 740 of the housing 712.

The rotatable sleeve 732a may be configured to rotate relative to the housing 712 between a first rotational position and a second rotational position gradually over the duration of the preselected time period. In some embodiments, the rotational motion of the rotatable sleeve 732a may be accomplished via a spring-based mechanism, such as, for example, a mechanism driven by a torsion spring. In the first rotational position, only the first portion 732c of the rotatable sleeve 732a may be rotationally aligned with the opening 732b formed in the proximal end 740 of the housing 712, as illustrated in FIG. 15A. Accordingly, when looking through the opening 732b, the patient or user may see the first color of the first portion 732c of the rotatable sleeve 732a. The first color may indicate to the patient or user that the injector 710 is unused and/or ready for initiation of the timer. As the rotatable sleeve 732a rotates in the counterclockwise direction in response to initiation of the timer, the second portion 732d of the rotatable sleeve 732a may gradually start to come into view through the opening 732b. The gradual increase in the proportion of the opening 732b occupied by the second color of the second portion 732d of the rotatable sleeve 732a may indicate to the patient or user that the end of the preselected time period is approaching. In the second rotational position, corresponding to the end of the preselected time period, only the second portion 732d of the rotatable sleeve 732a may be rotationally aligned with the opening 732b formed in the proximal end 740 of the housing 712, as illustrated in FIG. 15C. As a consequence, when looking through the opening 732b, the patient or user may only see the second color of the second portion 732d of the rotatable sleeve 732a. This may indicate to the patient or user that the preselected time period has elapsed, such that patient or user knows that the time has arrived for using the injector 710 to inject the drug.

Figure 16C:
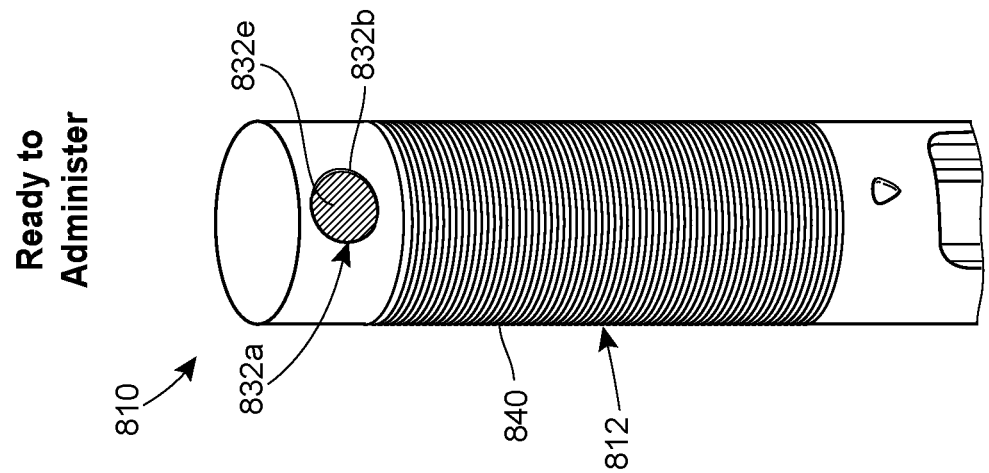
FIG. 16C is a perspective view of the injector of FIG. 16A after the preselected time period has elapsed.
Figure 16B:
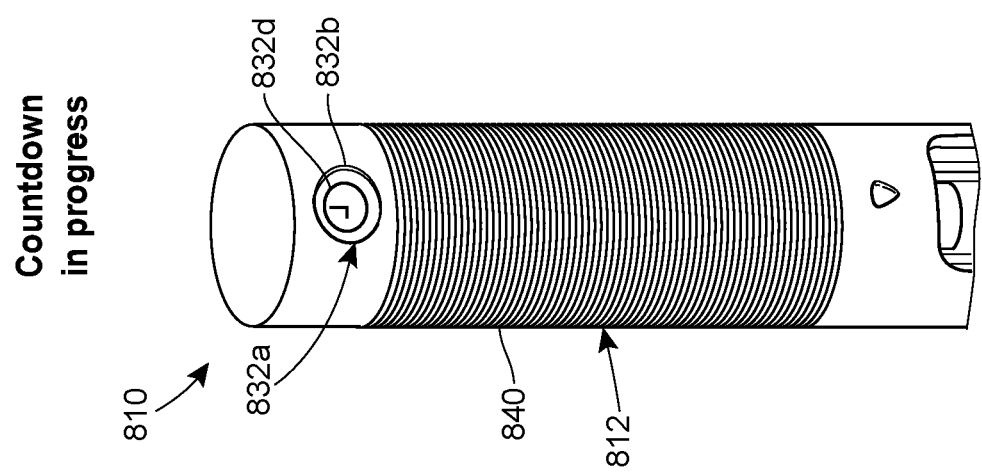
FIG. 16B is a perspective view of the injector of FIG. 16A during the preselected time period.
Figure 16A:
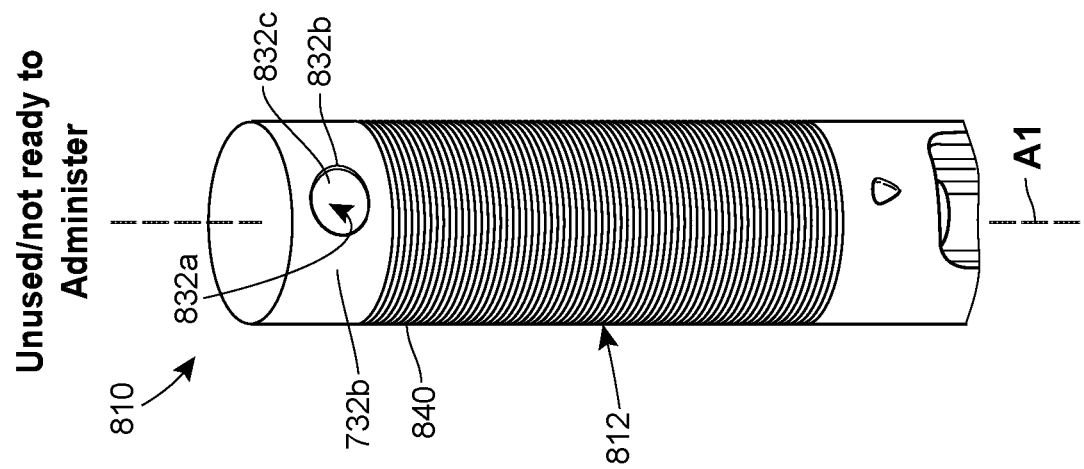
FIG. 16A is a perspective view of another embodiment of a system including an injector in accordance with principles of the present disclosure, prior to the start of a preselected time period.

FIGS. 16A-16C illustrate another embodiment of an injector 810 wherein the output element is defined at least in part by a rotatable sleeve 832a disposed in the interior space 852 of the housing 812 and which is rotatable around the longitudinal axis A1 of the housing 812. An opening 832b may be formed in a circumferential wall of the housing 812. The rotatable sleeve 832a may be positioned behind the opening 832b, such that the rotatable sleeve 832a is aligned along the longitudinal axis A1 of the housing 812 with the opening 832b. A first portion 832c of a circumferential outer surface of the rotatable sleeve 832a may have a first color or marking, a second portion 832d of the circumferential outer surface of the rotatable sleeve 832a may have a second color or marking, and a third portion 832d of the circumferential outer surface of the rotatable sleeve 832a may have a third color or marking. The first, second, and third colors and/or markings may each be different from each other to communicate different things to the patient or user. In some embodiments, the first color may be white and/or the same as a color of an exterior surface of the proximal end 840 of the housing 812; the second color or marking may be black and include the symbol of a clock (see FIG. 16B); and the third color may be green and/or differ from the color of the exterior surface of the proximal end 840 of the housing 812.

The rotatable sleeve 832a may be configured to rotate relative to the housing 812 between three discrete rotational positions over the duration of the preselected time period. The transition between the first and second rotational positions and between the second and third rotational positions may be instantaneous instead of being gradual. In some embodiments, the rotational motion of the rotatable sleeve 832a may be accomplished via a spring-based mechanism, such as, for example, a mechanism driven by a torsion spring. In the first rotational position, only the first portion 832c of the rotatable sleeve 832a may be rotationally aligned with the opening 832b formed in the proximal end 840 of the housing 812, as illustrated in FIG. 16A. Accordingly, when looking through the opening 832b, the patient or user may see the first color or marking associated with the first portion 832c of the rotatable sleeve 832a. The first color may indicate to the patient or user that the injector 810 is unused and/or ready for initiation of the timer. Upon initiation of the timer, the rotatable sleeve 832a may rotate instantaneously or very quickly to the second rotational position and then stop rotating. In the second rotational position, only the second portion 832d of the rotatable sleeve 832a may be rotationally aligned with the opening 832b formed in the proximal end 840 of the housing 812, as illustrated in FIG. 16B. Accordingly, when looking through the opening 832b, the patient or user may see the second color or marking associated with the second portion 832d of the rotatable sleeve 832a. The second color may indicate to the patient or user that the countdown of the preselected time period is underway and/or that the patient or user needs to wait to use the injector 810 for injecting the drug. After the elapse of the preselected time period, the rotatable sleeve 832a may rotate instantaneously or very quickly to the third rotational position and then stop rotating. In the third rotational position, only the third portion 832e of the rotatable sleeve 832a may be rotationally aligned with the opening 832b, as illustrated in FIG. 16C. As a consequence, when looking through the opening 832b, the patient or user may see the third color or marking associated with the third portion 832e of the rotatable sleeve 832a. This may indicate to the patient or user that the preselected time period has elapsed, such that patient or user knows that the time has arrived for using the injector 810 to inject the drug.

While the foregoing embodiments of the injector have been described in the context of an autoinjector or a device that is held in the patient or user's hand over the course of drug delivery, the scope of the present disclosure is not limited to such hand-held devices. In alternative embodiments, the injector may be releasably attached to the patient's skin such that the injector can be worn on the patient's skin during drug delivery, instead of being held in the patient's hand. Such an injector is referred to in some contexts as an on-body injector. On-body injectors can be useful where drug delivery is to occur over tens of seconds, minutes, or hours, and/or in situations where holding the injector in one's hand over the entire duration of drug delivery is not practical. In such embodiments, an exterior surface of the housing of the injector may include an adhesive for adhering to the patient's skin. Furthermore, in such embodiments, the injector may have a generally low-profile shape (e.g., a rectangular box) such that the injector does not impede the patient's movement while it is worn by the patient. A low-profile shape may be facilitated by having the longitudinal axis of the delivery member, or at least the pointed end of the delivery member, arranged perpendicular or otherwise non-parallel to the longitudinal axis of the reservoir and/or the longitudinal axis of the housing. Furthermore, the opening in the housing through which the pointed end of the delivery member extends in the delivery state may be covered by a pierceable septum for sterility purposes. In the initial state, the pointed end of the delivery member may not pierce through, or may pierce only partially through, this septum; whereas, in the delivery state, the pointed end of the delivery member may pierce entirely through the septum for insertion into the patient. Furthermore, in an on-body injector configurations of the injector, the delivery member may be defined by the combination of a hollow or solid trocar and a soft cannula. During operation, the trocar may be deployed to introduce the soft cannula into that patient and then retracted leaving the soft cannula within the patient's body. Except where differences in operation or structure require otherwise, such on-body injector configurations of the injector may incorporate a same or similar type of lockout system and/or output element as those described above in connection with the autoinjector configurations of the injector.

In still further alternative embodiments, the energy source may be omitted such that the patient or user is required to manually actuate the reservoir to deliver the drug. In such alternative embodiments, the injector may be a conventional syringe configured with one of the foregoing embodiments of the output element, where appropriate.

As will be recognized, the systems, devices, and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

Drug Information

As mentioned above, the reservoir of the injector may be configured to receive a volume of a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-

452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005)

and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No.

7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/Ilia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery systems and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A system for delayed delivery of a drug, comprising:
   a housing having an interior surface and an exterior surface, the interior surface defining an interior space;
   a delivery member configured to have an initial state, wherein the delivery member is withdrawn inside the interior space of the housing, and a delivery state, wherein a pointed end of the delivery member extends beyond the exterior surface of the housing for insertion into a patient;
   a reservoir configured to receive a volume of a drug and to be in fluid communication with the delivery member;
   an energy source activatable by the patient or a user to actuate the reservoir to deliver the volume of the drug to the patient as a single bolus; and
   a lockout system configured to have a locked state prior to a first use of the system to deliver the drug to the patient, wherein the lockout system prevents movement of the delivery member relative to the housing and/or activation of the energy source, and an unlocked state, wherein the lockout system permits movement of the delivery member relative to the housing and/or activation of the energy source, the lockout system being configured to automatically change from the locked state to the unlocked state after a preselected time period has elapsed.

2. The system of claim 1, the lockout system being configured to determine whether the preselected time period has elapsed.

3. The system of claim 2, the lockout system being configured to determine, only once, whether any preselected time period has elapsed.

4. The system of claim 2, comprising:
   an output element configured to generate a detectable output after at least one condition has been satisfied to notify the patient or the user of the satisfaction of the at least one condition; and
   wherein the at least one condition comprises the preselected time period, and the output element is configured to generate the detectable output after the lockout system has determined that the preselected time period has elapsed.

5. The system of claim 1, the lockout system including a timer for determining whether the preselected time period has elapsed.

6. The system of claim 5, the timer being configured with the preselected time period prior to being disposed within the interior space of the housing.

7. The system of claim 5, the timer including a spring configured to have an energized state at a beginning of the preselected time period and a de-energized state at an end of the preselected time period.

8. The system of claim 5, the timer being programmed into a memory device disposed within the interior space of the housing.

9. The system of claim 5, comprising an initiator connected to or in communication with the timer and permitting the patient or the user to initiate the timer, wherein a length of the preselected time period cannot be adjusted by the patient or the user.

10. The system of claim 9, the initiator permitting the patient or the user to initiate the timer only once.

11. The system of claim 1, comprising:
    a trigger member configured to move relative to the housing upon application of a force by the patient or the user, wherein movement of the trigger member activates the power source; and
    the lockout system including a resistance unit configured to resist movement of the trigger member relative to the housing in the locked state, and permit movement of the trigger member relative to the housing in the unlocked state.

12. The system of claim 1, wherein the housing comprises a sleeve and a guard member configured to move with respect to the sleeve, and wherein the pointed end of the delivery member is disposed outside of the guard member in the delivery state.

13. A system for delayed delivery of a drug, comprising:
    a delivery member configured for insertion into a patient;
    a reservoir configured to receive a volume of the drug and to be in fluid communication with the delivery member;
    an actuator configured to expel the volume of the drug from the reservoir to the patient via the delivery member as a single bolus;
    an output element configured to generate a detectable output after at least one condition has been satisfied to notify the patient or a user of the satisfaction of the at least one condition; and
    wherein the at least one condition comprises a preselected time period, and the output element is configured to generate the detectable output after a timer has determined that the preselected time period has elapsed prior to use of the system to deliver any drug to the patient.

14. The system of claim 13, the timer being configured with the preselected time period prior to use by the patient or the user.

15. The system of claim 13, the timer being configured such that a length of the preselected time period cannot be adjusted by the patient or the user.

16. The system of claim 15, the timer being configured to, only once, determine whether any preselected time period has elapsed.

17. The system of claim 13, comprising an initiator connected to or in communication with the timer and configured to permit the patient or the user to initiate the timer, wherein a length of the preselected time period cannot be adjusted by the patient or the user.

18. The system of claim 17, comprising:
a housing including an exterior surface and an interior surface, the interior surface defining an interior space; and
wherein delivery member is configured to have an initial state, wherein the delivery member is withdrawn inside the interior space of the housing, and a delivery state, wherein a pointed end of the delivery member extends beyond the exterior surface of the housing for insertion into the patient.

19. A system for delayed delivery of a drug, comprising:
a housing having an interior surface and an exterior surface, the interior surface defining an interior space;
a delivery member configured to have an initial state, wherein the delivery member is withdrawn inside the interior space of the housing, and a delivery state, wherein a pointed end of the delivery member extends beyond the exterior surface of the housing for insertion into a patient;
a reservoir configured to receive a volume of a drug and to be in fluid communication with the delivery member;
an energy source activatable by the patient or a user to actuate the reservoir to deliver the volume of the drug to the patient as a single bolus;
a lockout system configured to have a locked state prior to a first use of the system to deliver the drug to the patient, wherein the lockout system prevents movement of the delivery member relative to the housing and/or activation of the energy source, and an unlocked state, wherein the lockout system permits movement of the delivery member relative to the housing and/or activation of the energy source, the lockout system being configured to automatically change from the locked state to the unlocked state after a preselected time period has elapsed; and
the lockout system including a timer for determining whether the preselected time period has elapsed.

20. A system for delayed delivery of a drug, comprising:
a housing having an interior surface and an exterior surface, the interior surface defining an interior space;
a delivery member configured to have an initial state, wherein the delivery member is withdrawn inside the interior space of the housing, and a delivery state, wherein a pointed end of the delivery member extends beyond the exterior surface of the housing for insertion into a patient;
a reservoir configured to receive a volume of a drug and to be in fluid communication with the delivery member;
an energy source activatable by the patient or a user to actuate the reservoir to deliver the volume of the drug to the patient as a single bolus;
a lockout system configured to have a locked state prior to a first use of the system to deliver the drug to the patient, wherein the lockout system prevents movement of the delivery member relative to the housing and/or activation of the energy source, and an unlocked state, wherein the lockout system permits movement of the delivery member relative to the housing and/or activation of the energy source, the lockout system being configured to automatically change from the locked state to the unlocked state after a preselected time period has elapsed;
a trigger member configured to move relative to the housing upon application of a force by the patient or the user, wherein movement of the trigger member activates the power source; and
the lockout system including a resistance unit configured to resist movement of the trigger member relative to the housing in the locked state, and permit movement of the trigger member relative to the housing in the unlocked state.

* * * * *